(12) United States Patent
Baber et al.

(10) Patent No.: US 12,086,314 B2
(45) Date of Patent: Sep. 10, 2024

(54) SYSTEMS AND METHODS THAT INVOLVE BCI (BRAIN COMPUTER INTERFACE), EXTENDED REALITY AND/OR EYE-TRACKING DEVICES, DETECT MIND/BRAIN ACTIVITY, GENERATE AND/OR PROCESS SALIENCY MAPS, EYE-TRACKING INFORMATION AND/OR VARIOUS CONTROL(S) OR INSTRUCTIONS, IMPLEMENT MIND-BASED SELECTION OF UI ELEMENTS AND/OR PERFORM OTHER FEATURES AND FUNCTIONALITY

(71) Applicant: MindPortal, Inc., San Francisco, CA (US)

(72) Inventors: Jack Baber, London (GB); Ekram Alam, London (GB)

(73) Assignee: MindPortal, Inc., San Francisco, CA (US)

( * ) Notice: Subject to any disclaimer, the term of this patent is extended or adjusted under 35 U.S.C. 154(b) by 0 days.

(21) Appl. No.: 18/375,517

(22) Filed: Sep. 30, 2023

(65) Prior Publication Data
US 2024/0053825 A1    Feb. 15, 2024

Related U.S. Application Data

(63) Continuation of application No. PCT/US2023/030184, filed on Aug. 14, 2023.

(60) Provisional application No. 63/397,399, filed on Aug. 12, 2022, provisional application No. 63/397,398, filed on Aug. 12, 2022.

(51) Int. Cl.
G06F 3/01    (2006.01)

(52) U.S. Cl.
CPC .............. G06F 3/015 (2013.01); G06F 3/013 (2013.01)

(58) Field of Classification Search
CPC ........ G06T 19/006; G06F 3/013; G06F 3/015
See application file for complete search history.

(56) References Cited

U.S. PATENT DOCUMENTS

| | | | |
|---|---|---|---|
| 2017/0035317 A1* | 2/2017 | Jung | A61B 3/0025 |
| 2020/0069209 A1* | 3/2020 | Keane | A61B 5/38 |

* cited by examiner

Primary Examiner — Abbas I Abdulselam
(74) Attorney, Agent, or Firm — Greenberg Traurig, LLP

(57) ABSTRACT

Systems and methods associated with mind/brain-computer interfaces are disclosed. Certain implementations may include or involve processes of collecting and processing brain activity data, such as those associated with the use of a brain-computer interface that enables, for example, decoding and/or encoding a user's brain functioning, neural activities, and/or activity patterns associated with thoughts, including sensory-based thoughts.

Consistent with various aspects of the disclosed technology, systems and methods herein include functionality whereby a user can hands-free select or click UI elements in a mixed reality environment or on a 2D computer, phone or other such screen. In some embodiments, the disclosed technology may involve a brain-interface that can decode where the user is looking (i.e., determine their visual attention) and also decode their intention to select or 'click' the UI element desired. The user's intention to select or 'click' the UI element (the 2nd step) can be achieved through an imagined movement or an imagined word.

20 Claims, 28 Drawing Sheets

Individual Optode Module

Example Showing All Channels

MindPortal Extended Optode Configuration Technical Details

Sources
$32 * 2\lambda = 64$
Therefore, 4 * TLC5940 (16 chan)

Detectors
16
Therefore, 2 * ADS1299 (8 chan)

Concerns
Pyboard D

Options
Use STM Device Kit
Integrate it

| Sample Rate | / 60 |
|---|---|
| 1000 | 17 |
| 2000 | 33 |
| 4000 | 67 |
| 16000 | 270 |

- ⊗ Source (Dual-Wavelength) x 32
- ▨ Detector (PD w/ TIA) x 16
- ⬠ 30mm Channel x 50
- △ 21mm Channel x 30
- ▽ 47mm Channel x 27

$\Sigma = 107$

Individual Module

Another Illustrative Example

SYSTEMS AND METHODS THAT INVOLVE BCI (BRAIN COMPUTER INTERFACE), EXTENDED REALITY AND/OR EYE-TRACKING DEVICES, DETECT MIND/BRAIN ACTIVITY, GENERATE AND/OR PROCESS SALIENCY MAPS, EYE-TRACKING INFORMATION AND/OR VARIOUS CONTROL(S) OR INSTRUCTIONS, IMPLEMENT MIND-BASED SELECTION OF UI ELEMENTS AND/OR PERFORM OTHER FEATURES AND FUNCTIONALITY

CROSS-REFERENCE TO RELATED APPLICATIONS AND INCORPORATION INFORMATION

This is a continuation (bypass) of PCT International Application No. PCT/US23/30184, filed Aug. 14, 2023, published as WO, which claims benefit of/priority to U.S. provisional patent application No. 63/397,398, filed Aug. 12, 2022, and No. 63/397,399, filed Aug. 12, 2022, which are incorporated herein by reference in entirety.

DESCRIPTION OF RELATED INFORMATION

Conventionally, one significant challenge in the general field of brain-computer interfaces lies in the absence of options that are non-invasive and/or effective with regard to the interfaces that are in simultaneous communication with both neurons (e.g., a brain) and computing systems. For instance, as illustrated in FIG. 1A, a conventional electroencephalography (EEG) device may be attached to the scalp of a human to detect/collect brainwave related electrical activities of the user's brain. As shown herein, on the data collecting side, the EEG device 110 may be coupled via thin wires to the human scalp by an array of electrodes that include small metal discs 105 attached (e.g., pasted using conductive gel, etc.) onto the scalp. On the other side, a computing system 115 may be configured to provide on a monitor to display button A and button B. In this setup, button A is controlled to flash at a frequency A, and button B is controlled to flash at a frequency B that is different from the frequency A. When the user looks at button A, the brain generates neural signals different than those when the user looks at button B. As such, when the user looks at button A, the corresponding brain signals are detected at the EEG device 110 for transmission to the computing system 110, based on what occurs when button A is selected. However, in this conventional approach, the EEG device can only collect data at a very poor resolution and/or signal to noise rate or ratio. Further, only discrete applications are enabled using this technique to distinguish binary data in terms of, for example, yes versus no, green versus red, left versus right, and the like. As the human mind and its manifest expressions are much richer than dichotomized information, such limited application of a brain-computer interface does not lend itself to natural (e.g., more nuanced) use cases. Furthermore, training times for machine learning algorithms that allow the brain-computer interface to associate the brain signals with the respective button (A or B) with working accuracy can take unacceptable amounts of time.

FIG. 1B shows an example system using an invasive brain-computer interface. As shown in FIG. 1B, an invasive brain-computer interface 125 may also theoretically be implanted directly into a brain at one end, and transmit signals to an external device (e.g., a computing device 135) at another end. In this illustrated example, invasive brain-computer interface 125 may be implanted in the motor cortex (e.g., via surgery on a localized region, etc.) of the user's brain to detect neural signals associated with brain activities, such as thought patterns 130. Here, when the user imagines moving the right arm versus moving the left arm, the detected signals are transmitted to the computing device 135 to cause the computing device 135 to select a displayed right arrow versus to select a displayed left arrow. With this approach, the brain-computer interface can only register neural patterns from the portion of the brain in which electrodes or other sensors have been implanted and therefore cannot decode all the senses of the user and use cases are generally limited to medical patients only (e.g., augmenting vision, hearing impaired sensory abilities, etc.) due to the support requirements for maintaining an invasive interface.

Overview of Some Aspects of the Disclosed Technology

Systems and methods associated with mind/brain-computer interfaces are disclosed. Embodiments herein include features related to one or more of optical-based brain signal acquisition, decoding modalities, encoding modalities, brain-computer interfacing, and/or AR/VR content interaction, among other features set forth herein. Certain implementations may include or involve processes of collecting and processing brain activity data, such as those associated with the use of a brain-computer interface that enables, for example, decoding and/or encoding a user's brain functioning, neural activities, and/or activity patterns associated with thoughts, including sensory-based thoughts.

Consistent with various aspects of the disclosed technology, systems and methods herein include features and functionality whereby a user can hands-free select or click UI elements in a mixed reality environment or on a 2D computer, phone or other such screen. According to some embodiments, the disclosed technology may use or involve a brain-interface which can decode where the user is looking (i.e., determine their visual attention) and also decode their intention to select or 'click' the UI element desired. The user's intention to select or 'click' the UI element (the 2nd step) can be achieved through an imagined movement or an imagined word.

In certain illustrative implementations, for example, a user performs steps to enable certain innovations herein to be achieved: (1) looking at or viewing the UI element (in VR, AR or on a 2D screen) that they are interested in, and (2) intending to select/click the UI element (either by imagining a clicking movement of their finger or hand or by imagining a word in their mind such as 'click' or 'yes'). Both of those steps must be completed in order to make a selection, and the combination of the two as set forth herein achieves various innovative results and benefits. In addition, embodiments of the disclosed technology may include a novel method for step 1, which uses brain data derived from the visual areas of the brain to determine where they are focused on with their eyes. Further, embodiments of the disclosed technology may include a novel method for step 2, which uses brain data derived from language areas of the brain to decode a word they are imagining in their mind such as 'yes' or 'click' to make the selection occur on the UI.

These and other innovations herein overcome various drawbacks in the art. For example, if the user only looks at something, it will not select a desired object. This is the key problem from before this technology—eye tracking alone makes for a frustrating way of selecting things on a screen, because the only way it can work is through dwell time or how long a user looks at the item. If you set this variable to too short a time, you end up selecting everything you glance at on a screen. But if you set the variable to a longer time than this, it causes eyestrain and feels slow for a user.

As set forth in various illustrative embodiments described below, the present disclosure provides examples of technically improved computer-based processes, systems and computer program products associated with or involving a brain-computer interface based platform that decodes and/or encodes neural activities associated with thoughts (e.g., human thoughts, etc.), user motions, and/or brain activity based on signals gathered from location(s) where brain-detection optodes are placed. These optodes, which will be described in greater detail below, may operate in sensory modalities such as vision, speech, sound, gesture, movement, actuation, touch, smell, and the like. According to some embodiments, the disclosed technology may include or involve process for detecting, collecting, recording, and/or analyzing brain signal activity, and/or generating output(s) and/or instructions regarding various data and/or data patterns associated with various neural activities/activity patterns, all via a non-invasive brain-computer interface platform. Empowered by the improvements set forth in the wearable and associated hardware, optodes, etc. herein, as well as its various improved aspects of data acquisition/processing set forth below, aspects of the disclosed brain-computer interface technology can achieve high resolution activity tracking, physical portability, and/or enhanced data collecting ability, among other benefits and advantages. These systems and methods leverage numerous technological solutions and their combinations to create a novel brain-computer interface platform, wearable devices, and/or other innovations that facilitate mind/brain computer interactions to provide specialized, computer-implemented functionality, such as optical modules (e.g., with optodes, etc.), thought detection and processing, limb movement decoding, whole body continuous movement decoding, AR and/or VR content interaction, direct movement goal decoding, direct imagined speech decoding, touch sensation decoding, and the like.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments.

DETAILED DESCRIPTION OF ILLUSTRATIVE IMPLEMENTATIONS

Systems, methods and wearable devices associated with brain-computer interfaces are disclosed. Embodiments described herein include features related to optical-based brain signal acquisition, decoding modalities, encoding modalities, brain-computer interfacing, AR/VR content interaction, signal to noise ration enhancement, and/or motion artefact reduction, among other features set forth herein. Certain implementations may include or involve processes of collecting and processing brain activity data, such as those associated with the use of a brain-computer interface that enables, for example, decoding and/or encoding a user's brain functioning, neural activities, and/or activity patterns associated with thoughts, including sensory-based thoughts. Further, the present systems and methods may be configured to leverage brain-computer interface and/or non-invasive wearable device aspects to provide enhanced user interactions for next-generation wearable devices, controllers, and/or other computing components based on the human thoughts, brain signals, and/or mind activity that are detected and processed.

Figure 1A:
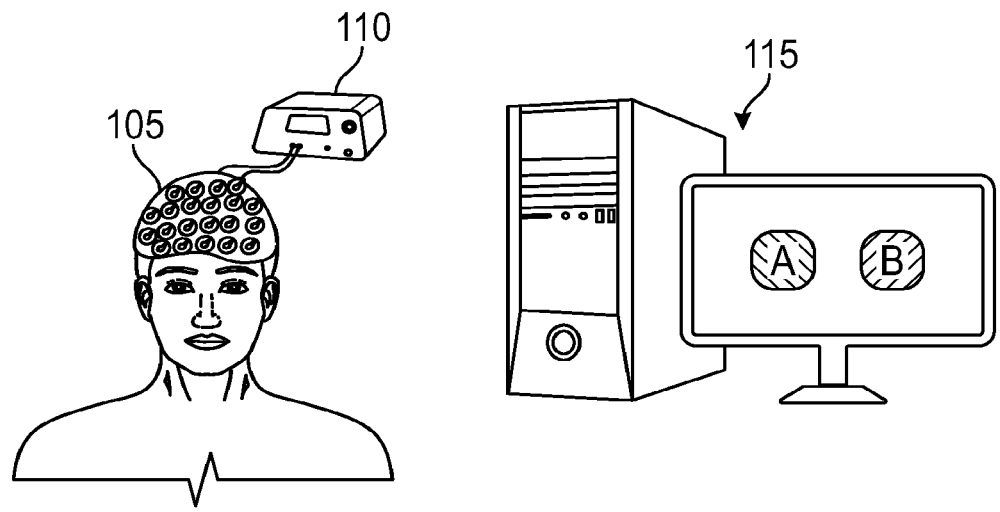
FIGS. 1A-1B describe traditional brain-computer interfaces (BCIs).
Figure 1B:
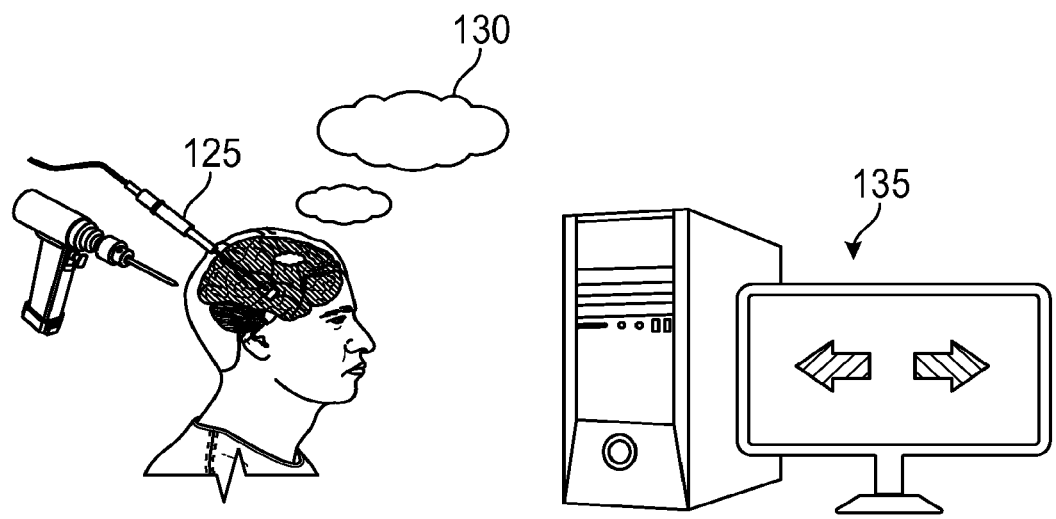
Figure 2A:
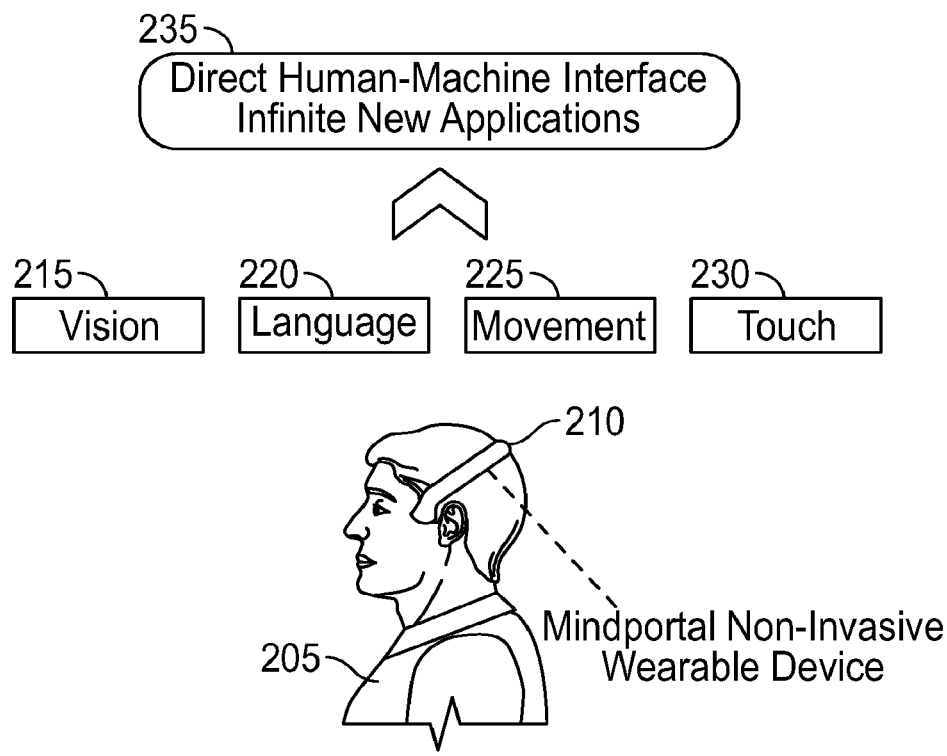
FIG. 2A is a diagram illustrating one exemplary process for decoding neural activities associated with human thoughts of manifesting sensory modalities, consistent with exemplary aspects of certain embodiments of the present disclosure.

FIG. 2A is a diagram illustrating one exemplary process related to decoding neural activities associated with human thoughts involving or manifesting sensory modalities, consistent with exemplary aspects of certain embodiments of the present disclosure. In this illustrated example, a human user 205 may wear a non-invasive and wearable device 210 that implements the brain computer interface (BCI) technology disclosed herein. As illustrated in FIG. 2A, device 210 may be configured to be positioned around the head/brain of the user so as to mount the scalp of the user. The BCI device 210 may also be configured to be worn in other suitable ways that do not require surgery on the user. When neural signals are detected/collected, device 210 may directly decode or translate neural activities of the user into machine-readable information. For example, neural activities of user 205 may be decoded by the BCI device 210 into vision 215 (e.g., mental images, etc.), language 220 (e.g., imagined speech, etc.), movement 225 (e.g., imagined body motions), touch 230 (e.g., imagined touch sensations), and other sensory modalities. Empowered with the sensory data decoded from the neural activities, a variety of applications 235 may be implemented via the BSI technology disclosed herein.

Figure 2B:
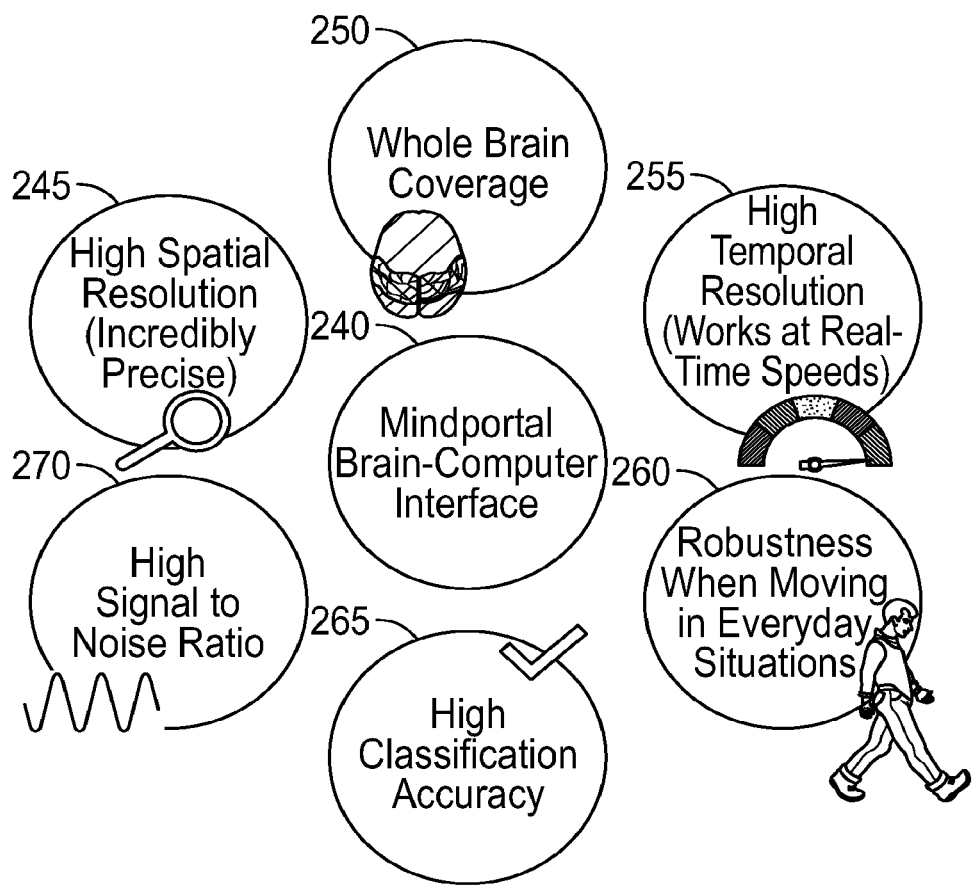
FIG. 2B is a diagram illustrating an exemplary BCI, consistent with exemplary aspects of certain embodiments of the present disclosure.

FIG. 2B is a diagram illustrating an exemplary brain computer interface 240 and various illustrative features, consistent with exemplary aspects of certain embodiments of the present disclosure. As shown in this figure, brain-computer interface 240 may be configured with various exemplary features and functionality such as ability to obtain neural activity data of high spatial resolution (e.g., highly precise) 245, obtain data spanning full brain coverage 250, obtain data of high temporal resolution (e.g., works at real-time speed/manner, etc.) 255, obtain data that is robust and accurate, e.g., when the user moves about in everyday situations, etc., at 260, obtain data of high classification accuracy 265, obtain data of high signal to noise ratio 270, and the like. As a result of these features and benefits, the brain-computer interface 240 may be configured to be worn by the user (or otherwise applied onto the user) in a more compelling and/or natural fashion.

Figure 3:
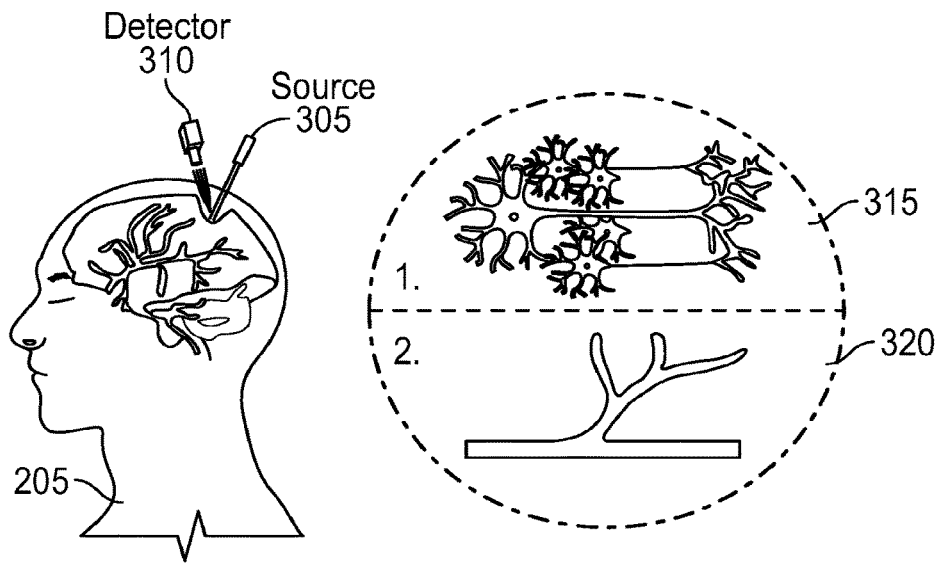
FIG. 3 depicts various exemplary aspects/principles involving detecting neural activities, consistent with exemplary aspects of certain embodiments of the present disclosure.

FIG. 3 depicts exemplary principles involved with detection of neural activities, consistent with exemplary aspects of certain embodiments of the disclosed technology. In this example, an optoelectronic based technique can be used to implement a brain-computer interface such as the one described in connection with FIGS. 2A-2B. In the example of FIG. 3, a detector 310 and a source 305 (e.g., an optical source, such as a laser light source, etc.) are applied to the brain of the user 205. As the brain incurs neural activities (e.g., thoughts, including but not limited to those of senses such as an image, sound, speech, movement, touch, smell, etc., upon body movement(s), and/or upon brain activity in certain locations, etc.), different regions of neurons in the brain are "activated" as manifested in, e.g., changes in neurons themselves, changes in blood supplies to the neurons, and so on. In this example, using optical system(s) herein, brain-computer interfaces consistent with the disclosed technology may be configured to detect: 1) neuronal changes, as illustrated in the upper half circle, at 315; and/or 2) blood changes at active site of the brain, as illustrated in the lower half circle, at 320.

Figure 4:
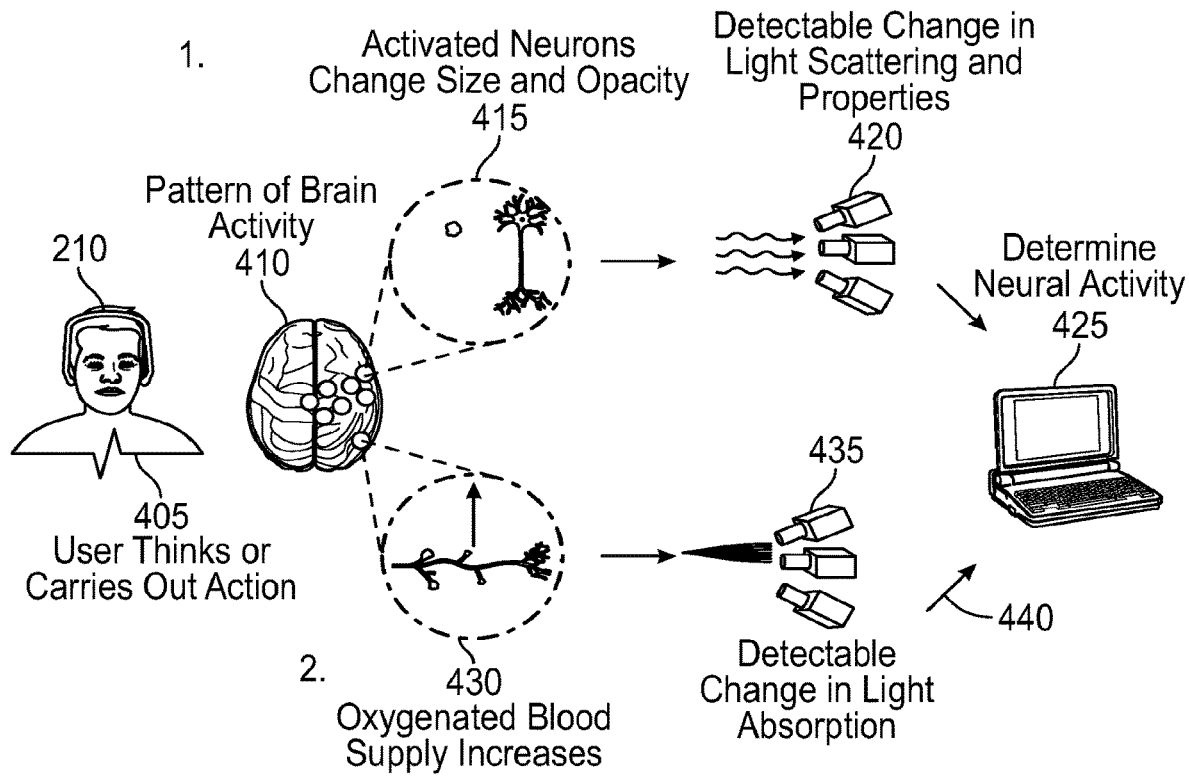
FIG. 4 depicts other exemplary aspects/processes involving detecting neural activities, consistent with exemplary aspects of certain embodiments of the present disclosure.

FIG. 4 is an exemplary flow diagram involving detection of neural activities, consistent with exemplary aspects of certain embodiments of the present disclosure. In this illustrated example, two possible pathways for communicating the user's thoughts to an external device are shown. Here, the user (shown with wearable device 210) thinks or carries out an action at step 405. Upon having such thoughts and/or performing such actions, wearable device 210 can detect pattern of brain activity 410. Along the upper pathway, such patterns of neuron activities may be manifested in, as shown at step 415, activated neuron change in size and/or opacity, and/or other characteristics associated with a neuron activation state. As such, at step 420, the patterns of brain activities may be detected (e.g., by use of the optodes configured on device 210, etc.) via detectable changes in light scattering and/or properties caused by the above-described physical changes in the activated neurons. In this illustrative implementation, at step 425, the detected signals are transmitted to an external device for further processing/application. Along the lower pathway via step 430, pattern of brain activity 410 may be manifested in an oxygenated blood supply increase and/or other blood flow and/or blood vessel characteristics associated with a neuron activation state. As such, at step 435, the patterns of brain activities may be detected (e.g., by use of the optodes configured on device 210, etc.) via detectable changes in light absorption. In turn, such detected signals may then be transmitted to the external device for further processing/application, at step 440. In some embodiments, the two pathways may also be reversed such that the brain-computer interface is a bi-directional and/or encoding interface that is capable of encoding signals (e.g., data, information of images, texts, sounds, movements, touches, smell, etc.) and transmitting these signals to the user's brain to invoke thoughts/actions based thereof. In some embodiments, the BCI may be configured to achieve signal detection precision level of 5 mm cubed, but the precision (spatial resolution) can be altered in order to extract information from brains of different volumes/sizes.

Figure 5:
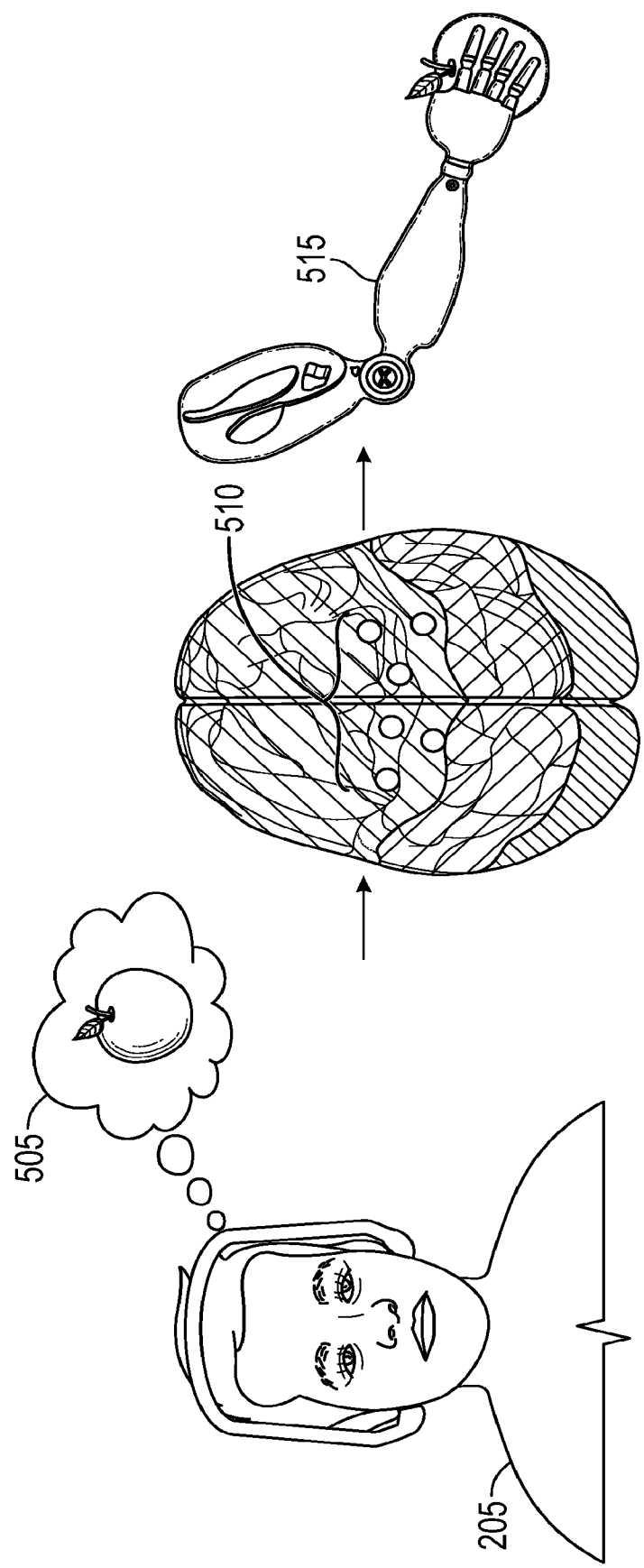
FIG. 5 is an exemplary application based on an exemplary BCI, consistent with exemplary aspects of certain embodiments of the present disclosure.

FIG. 5 depicts one illustrative application based on an exemplary brain-computer interface, consistent with exemplary aspects of certain embodiments of the present disclosure. In this example, a user equipped with a brain-computer interface can achieve a direct physical goal, such as retrieving an apple. As shown in FIG. 5, user 205 (wearing the BCI) contemplates a goal of picking up an apple in real and/or a virtual environment by, for example, thinking of picking up an apple, at step 505. As a result, the goal itself may produce neural activity/activity pattern 510 before the movement is planned in/implemented by the brain. With an associated brain-computer interface detecting the corresponding neural activities 510 in the user's brain, a robot (e.g., robotic arm, etc.) and/or a virtual arm (e.g., a virtual entity's modality) may be actuated to make its own movement to pick up an apple, at 515, in the respective environment, based on the goal as decoded from neural activities 510.

Figure 6:
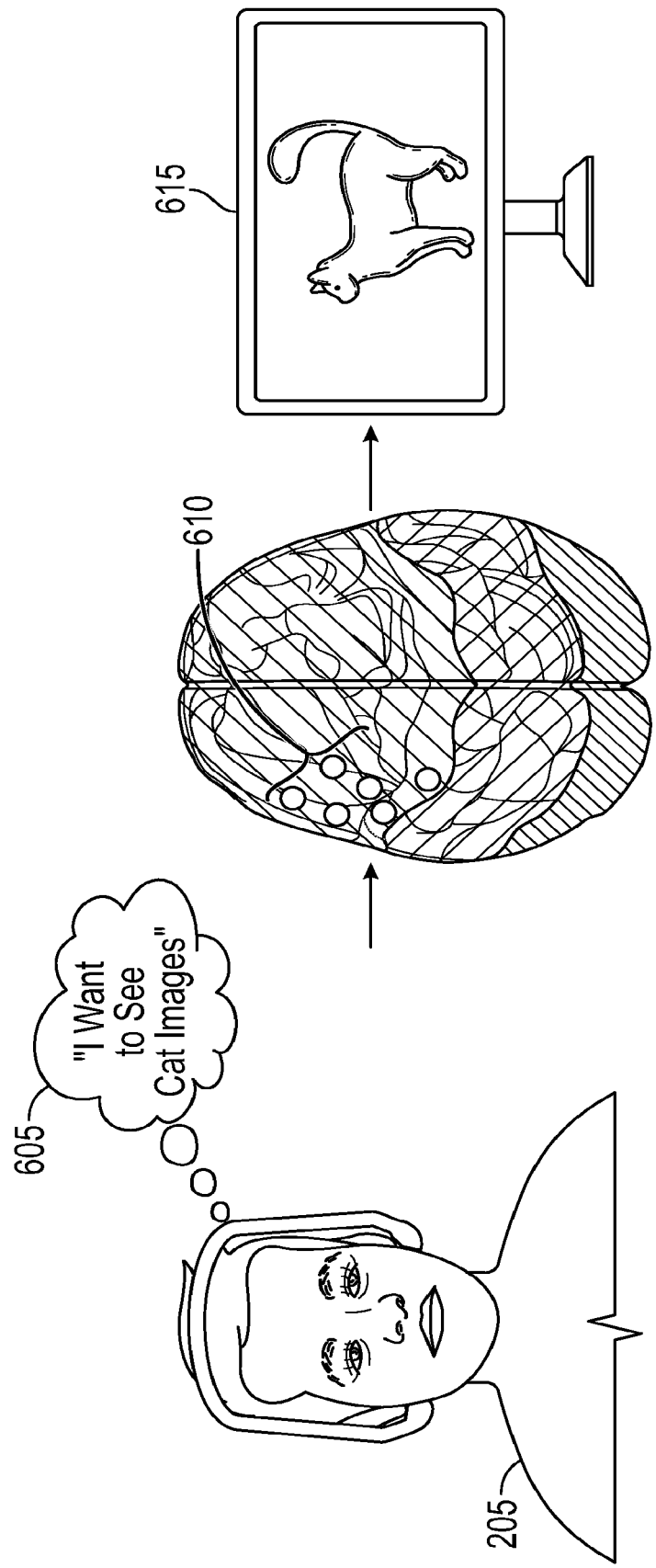
FIG. 6 is another exemplary application based on an exemplary BCI, consistent with exemplary aspects of certain embodiments of the present disclosure.

FIG. 6 depicts another illustrative application based on an exemplary brain-computer interface, consistent with exemplary aspects of certain embodiments of the present disclosure. In this example, a brain-computer interface is utilized to achieve a direct-imagined thought or speech of a user. Here, the user 205 (wearing the BCI) imagines semantic information, such as saying a sentence, a command or the like by thinking a thought 605 of, for example, "I want to see cat images." As a result, the neural activity/activity pattern 610 associated with the semantic information is incurred in the user's brain. With the BCI detecting the corresponding neural activities 610 in the user's brain, a software application may be configured to convert the imagined speech to text or to otherwise carry out the imagined command. Here, the software is illustrated to execute the imagined command, hence, here, displaying a cat image on a display monitor, at 615.

Figure 7:
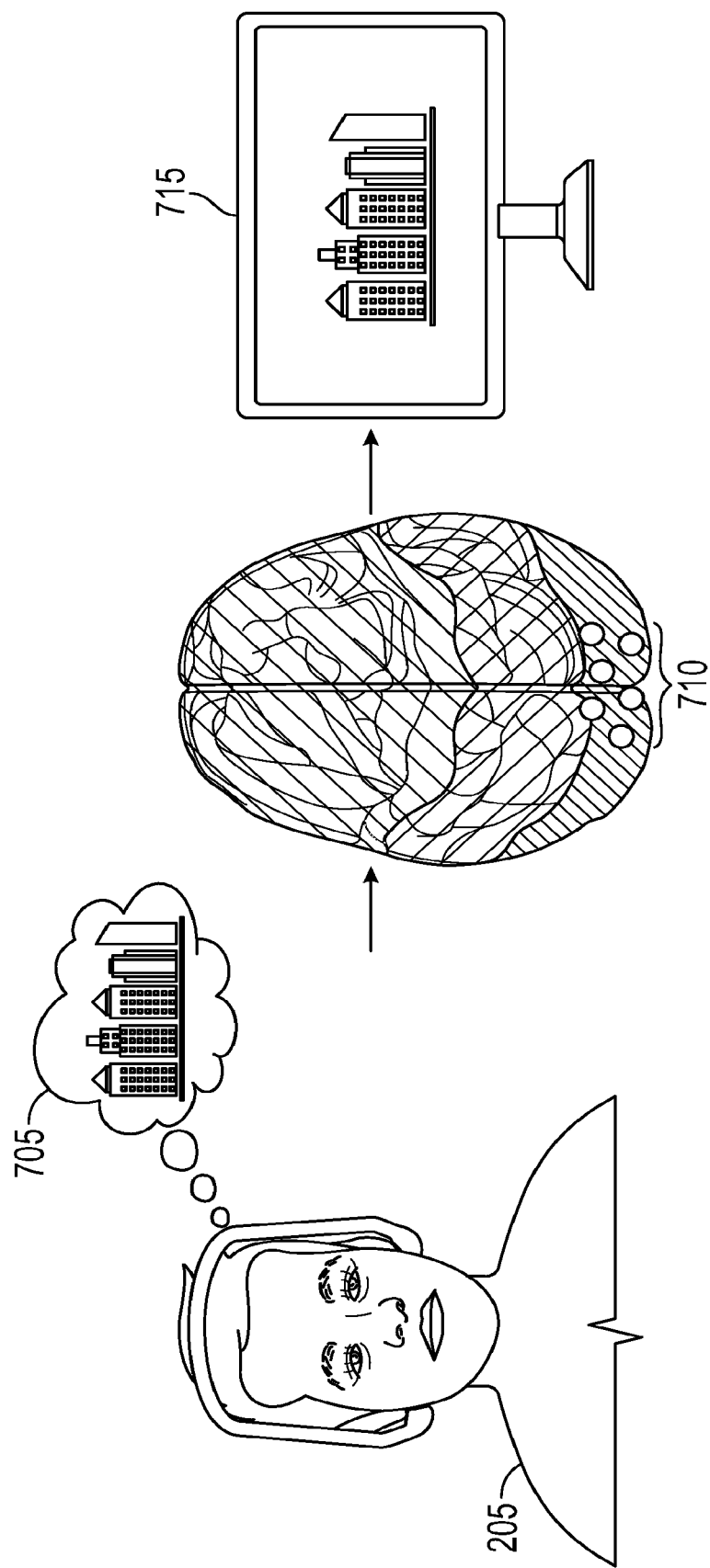
FIG. 7 is a further exemplary application based on an exemplary BCI, consistent with exemplary aspects of certain embodiments of the present disclosure.

FIG. 7 depicts another illustrative application based on an exemplary brain-computer interface, consistent with exemplary aspects of certain embodiments of the present disclosure. In this example, a BCI is utilized to achieve a direct transfer of the imagined visual images of a user to a machine. Here, user 205 (wearing the BCI) imagines visual information by thinking of, for example, a skyline (e.g., real and/or imaged/fictional) of a city (e.g., a real city and/or an imaged/fictional city), at step 705. As a result, the neural activity/activity pattern 710 associated with the imagined visual information is incurred in, for example, the visual cortex portion of the user's brain. With the brain-computer interface detecting the corresponding neural activity/activity pattern 710 in the user's brain, a software application may be configured to directly decode the neural activity pattern to allow the imagined image to be reconstructed and/or displayed on a visual interface, at step 715. In the present embodiment, for example, the software may decode and display the user's imagined visuals on a displaying monitor, as shown.

Figure 8:
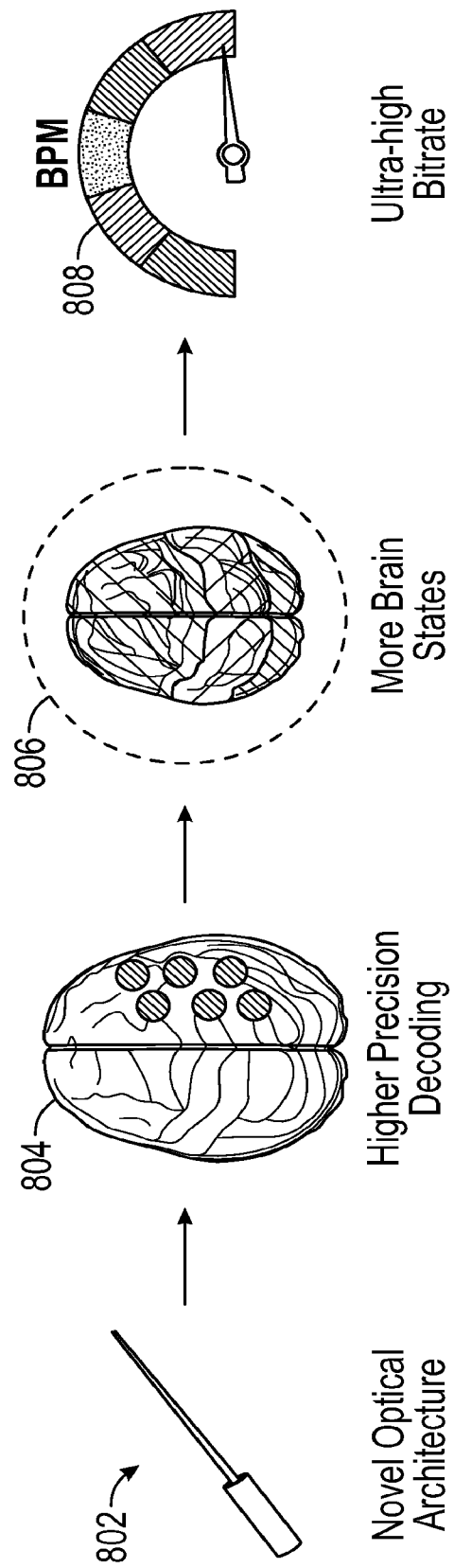
FIG. 8 is a flow diagram illustrating a simplified exemplary process, consistent with exemplary aspects of certain embodiments of the present disclosure.

FIG. 8 is a diagram illustrating another exemplary process flow, consistent with exemplary aspects of certain embodiments of the present disclosure. Here in this example, the disclosed novel optical architecture, at 802, is applied (in a non-invasive manner) to a user's brain to provide high/higher precision decoding, at 804. As such, more brain activities/brain states may be detected, at 806, which leads to enhanced bitrate in data collection/detection, etc., at 808.

Figure 9A:
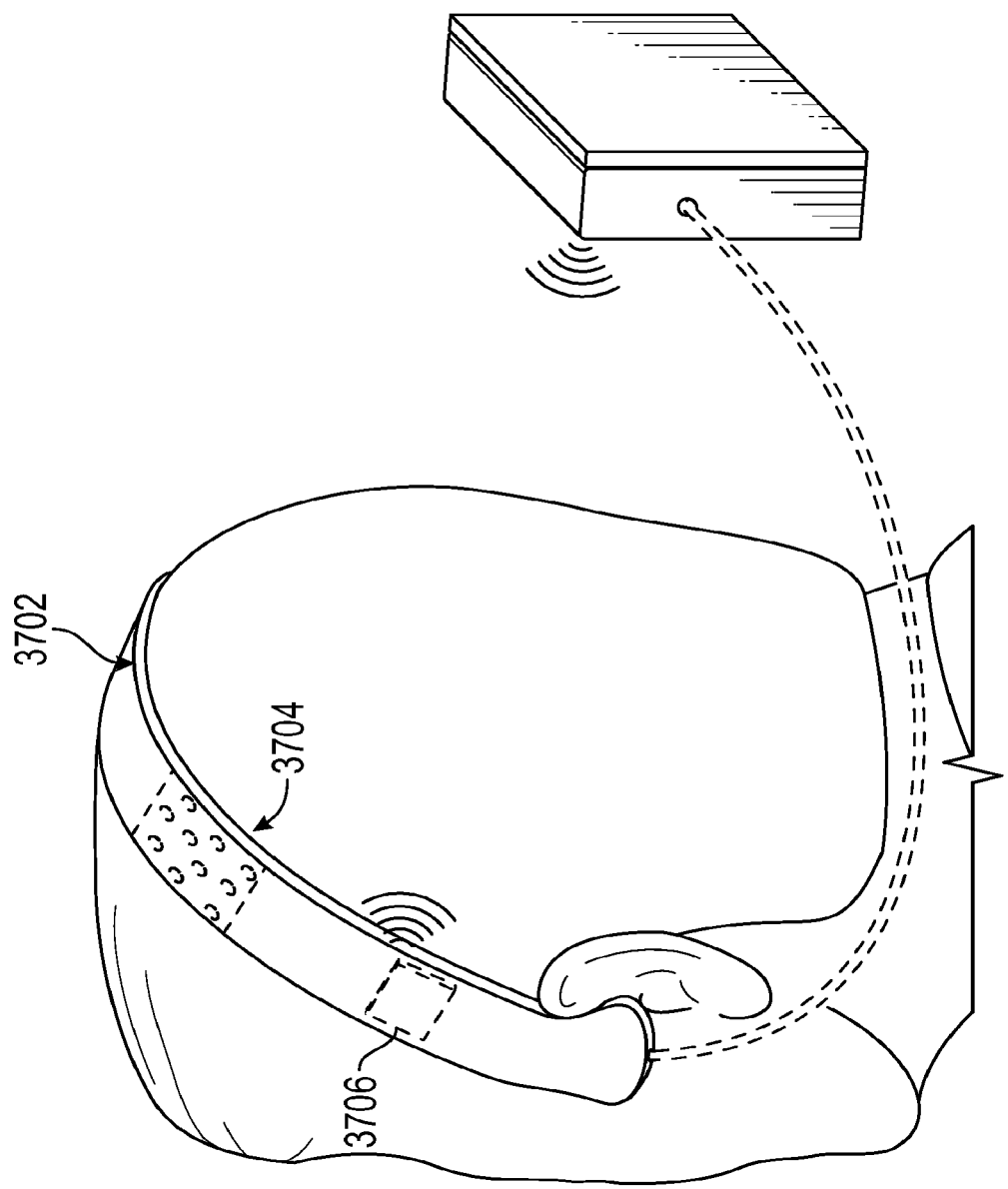
FIG. 9A is a diagram illustrating an exemplary wearable BCI device, consistent with exemplary aspects of certain embodiments of the present disclosure.

FIG. 9A is a diagram illustrating one exemplary wearable brain-computer interface device, consistent with exemplary aspects of certain embodiments of the present disclosure. As shown in this example, a wearable/portable brain-computer interface device ("BCI device") 902 may be configured to be worn by a user in a non-invasive manner. For example, BCI device 902 may be worn as a headband. In this example, the BCI device 902 is shown as mounted atop/across the user's head, with one or more brain-facing detection portions, panels or subcomponents 904 facing towards the user's brain. According to implementations herein, such brain-facing portions, panels or subcomponents 904 may include one or more optodes Each of these optodes can include one or more sources, such as dual-wavelength sources, and/or one or more detectors, such as photodiodes (e.g., in some exemplary embodiments, with integrated TIAs, transimpedance amplifiers, etc.). Examples of such sources and detectors are shown and described in more detail in connection with FIGS. 9C-9D and 10A through 11C, below. In the example of FIG. 9A, BCI device 902 may be adapted in any wearable shape or manner, including but not limited to the example embodiment shown here, having a curved and/or head-shaped design. In this example, the wearable devices (including BCI device 902) and/or subcomponents thereof (e.g., optodes and/or comparable sources and detectors) can be adapted to adjustably fit and cover the user's head such that the desired optodes (or equivalent) are positioned over the portion(s) of the user's brain to capture neural activity in specific regions of the user's brain. BCI device 902 may also be configured with one or more processing/computing subcomponents 906, which may be located on or in the wearable device itself. Alternatively, one or more of subcomponents 906 may be located outside of BCI device 902, physically and/or operationally/computationally, such as in a separate subcomponent and/or integrated with other computing/processing components of the disclosed technology. For example, the housing of subcomponents 906 may be placed on or in a wristband, watch, another such wearable, or other device. In some embodiments, subcomponents 906 can be connected to the remainder of the headset via a wireless or radio frequency connection, such as via Bluetooth or WiFi. Further, subcomponents 906 can include a housing which in this particular embodiment of a wearable is used to house the wiring and the electronic circuitry shown in FIG. 9B, including components such as, e.g., the optical source drivers 922, analog to digital converters 916, 920, and microcontroller and WiFi module 914.

Figure 9B:
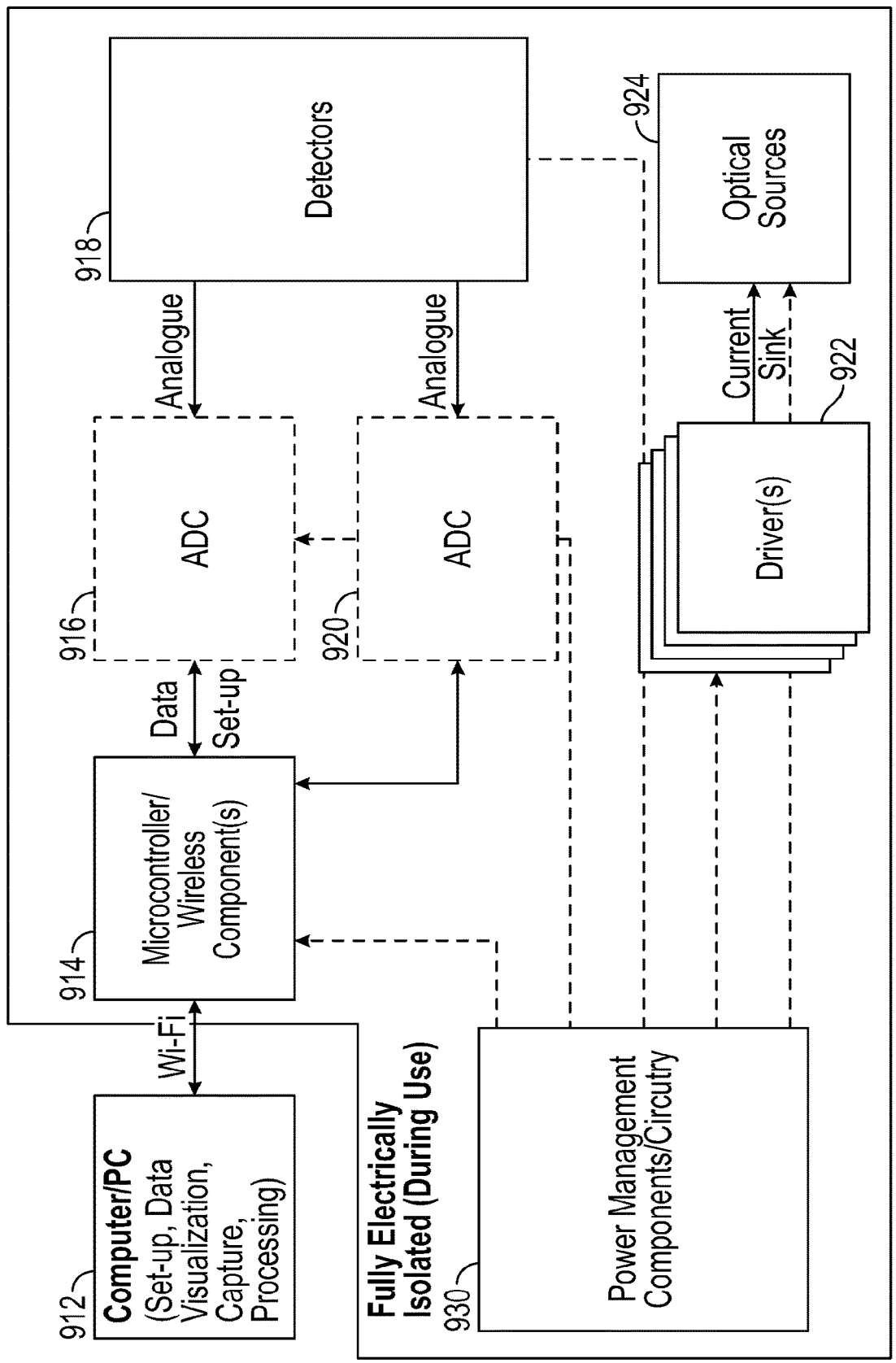
FIG. 9B is a block diagram illustrating components of an exemplary wearable BCI device, consistent with exemplary aspects of certain embodiments of the present disclosure.

FIG. 9B is a block diagram illustrating an exemplary brain-computer interface device, such as wearable device 902 shown in FIG. 9A and an associated computing device 912 (e.g., computer, PC, gaming console, etc.), consistent with exemplary aspects of certain embodiments of the present disclosure. As shown herein, an example brain-computer interface device can include: one or more one optical source driver(s) 922, which may, e.g., be utilized to control the intensity, frequency and/or wavelength of the optical signals emitted by the optical sources and may also be configured to set the electromagnetic energy to be emitted in continuous form or in timed pulses of various length or in other such frequency-type variations; at least one optical source 924 configured to emit the optical signal (e.g., light, laser, electro-magnetic energy, etc.), which, in some embodiments, may be in the near-infrared, infrared or visual range of the spectrum; one or more optional conversion components (illustrated as ADC 916, 920), if/as needed, such as analog to digital and/or digital to analog converters (ADC); one or more optical detectors 918 that detect optical signals that exit the brain tissue containing information regarding the properties of the brain of the human user; at least one microcontroller and/or WiFi module 914, where such microcontroller may be configured to sends control signals to activate the various components on the electronics layout and may also be configured to control the WiFi module. In some implementations, the microcontroller and/or WiFi module 914 may be connected to one or more computing components 912, such as a PC, other computing device(s), gaming consoles, and the like by one or both of a physical/hard-wire connection (e.g., USB, etc.) and/or via a wireless (e.g., WiFi, etc.) module. Further, the microcontroller and WiFi module may be housed together, as shown, they may be split or distributed, and one, both or neither may be integrated with a wearable BCI device, another mobile device of the user (e.g., watch, smartphone, etc.) and/or the other computing and/or PC device(s) 912.

According to one or more embodiments, in operation, the driver(s) 922 may be configured to send a control signal to drive/activate the light sources 922 at a set intensity (e.g., energy, fluence, etc.), frequency and/or wavelength, such that optical sources 924 emit the optical signals into the brain of the human subject.

Turning next to operations associated with detection and/or handling of detected signals, in some embodiments, various processing can occur using fast optical signals and/or haemodynamic measurement features, as will be described in greater detail below. In some embodiments, for example, one or both of such processing may be utilized, which may be carried out simultaneously (whether being performed simultaneously, time-wise, or in series but simultaneous in the sense that they are both performed during a single measurement sequence) or separately from one another:

In embodiments that utilize fast optical signal processing, an optical signal entering the brain tissue passes through regions of neural activity. As described above, changes in neuronal properties alter optical properties of brain tissue, causing the optical signal to scatter depending on an activation state and/or neural activity pattern, yielding a scattered signal. Further, such scattered light then serves as the optical signal that exits the brain tissue as an output signal, which is detected by the one or more detectors to be utilized as the received optical signal that is processed.

In embodiments that utilize haemodynamic analysis, optical signals entering brain tissue pass through regions of active blood flow near neural activity sites. As described above, changes in neuronal activation states and/or neural activity patterns can cause changes in blood flow that alter optical absorption properties of the brain tissue. The optical signal is then absorbed to a greater/lesser extent depending on these absorption properties, and, finally, the non-absorbed optical signal(s) exit brain tissue as an output signal, which is detected by the one or more detectors to be utilized as the received optical signal that is processed.

Turning to next steps or processing, the one or more detectors 918 detect optical signals which emerge from the human brain tissue. These optical signals may be converted, such as from analog to digital form or as otherwise needed, by one or more converters, such as one or more analog to digital converters 916, 920. Further, the resulting digital signals can be transferred to a computing component, such as a computer, PC, gaming console, etc. via the microcontroller and communication components (wireless, wired, WiFi module, etc.) for signal processing and classification.

Various other specific components of such exemplary wearable brain-computer interface device are also shown in the illustrative embodiment depicted in FIG. 9B, such as microcontroller/wireless component(s) 914 (which may include, e.g., a Pyboard D component), converters 916, 920 (which may include, e.g., ADS1299 ADC components), detectors 918 (which may include, e.g., an OPT101 component having photodiode with integrated TIA, etc.), optical sources 924 (which may, e.g., include laser sources, LEDs, etc.), driver(s) 922 (which may include, e.g., one or more TLC5940 components, etc.), and power management components/circuitry 930, though the innovations herein are not limited to any such illustrative subcomponents.

Figure 9D:
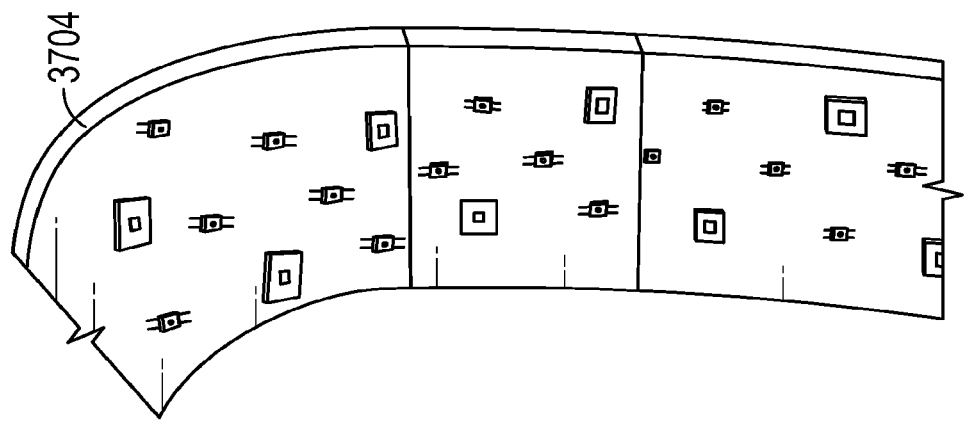
FIGS. 9C and 9D are schematic diagrams of example optode arrangements for an exemplary wearable BCI device, consistent with exemplary aspects of certain embodiments of the present disclosure.
Figure 9C:
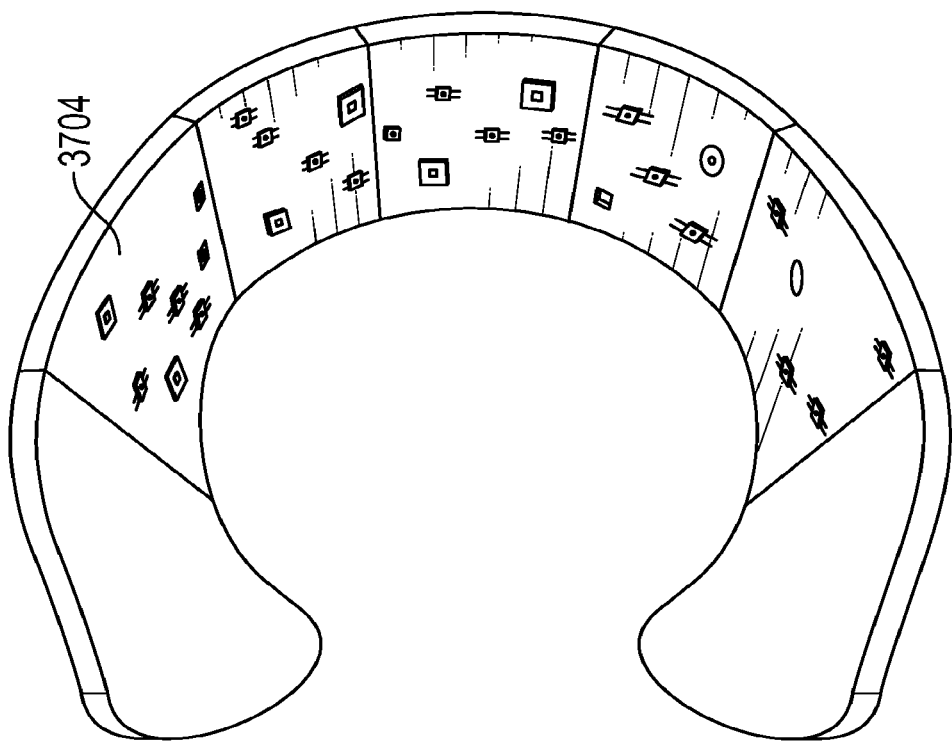

FIGS. 9C-9D are diagrams illustrating aspects of the one or more brain-facing detection portions, panels or subcomponents 904, consistent with exemplary aspects of certain embodiments of the present disclosure. As set forth in more detail elsewhere in other sections of this disclosure, such portions, panels or subcomponents 904 can include one or more panels, which each include one or more optodes 928. As set forth, below, each such optode can include one or more sources, such as dual-wavelength sources, and/or one or more detectors, such as photodiodes (e.g., in some exemplary embodiments, with integrated TIAs, transimpedance amplifiers, etc.), such as shown and described in more detail in connection with FIGS. 9C-9D and 10A through 11C, below.

Figure 10A:
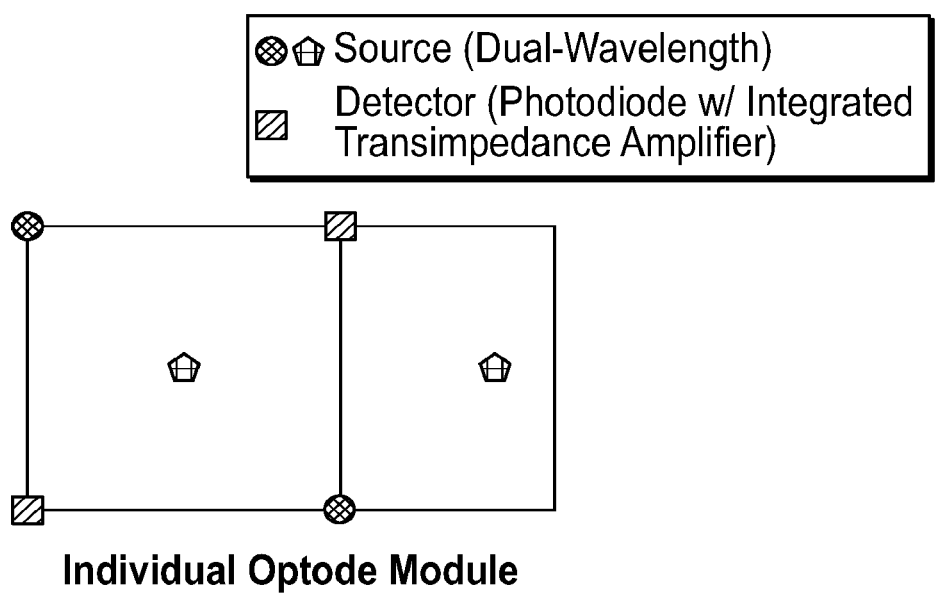
FIGS. 10A-10C depicts illustrative implementations regarding optode modules, consistent with various exemplary aspects of one or more implementations of the disclosed technology.

FIG. 10A is a representation depicting an illustrative optode module, consistent with various exemplary aspects of one or more implementations of the disclosed technology. Here, for example, rather than using individual sources and detectors, a wearable device or portion thereof may utilize a custom optode module, such as the exemplary optode module of FIG. 10A or elsewhere herein, that provides a number of benefits. As to one benefit, such optode modules may be shaped and configured to be placed adjacent to each other or otherwise repeated, which simplifies both construction (of the optodes and wearable) while also simplifying the process of increasing the number of channels.

According to certain implementations herein, an optode module or array may include 3-5 optical sources as well as 1-3 optical detectors. In the specific example of 10A, an optode module or array can include 4 dual-wavelength optical sources and 2 optical detectors that include a photodiode with an integrated transimpedance amplifier. Finally, in certain embodiments, at least one of the sources is positioned at or near center of the optode array.

Figure 10B:
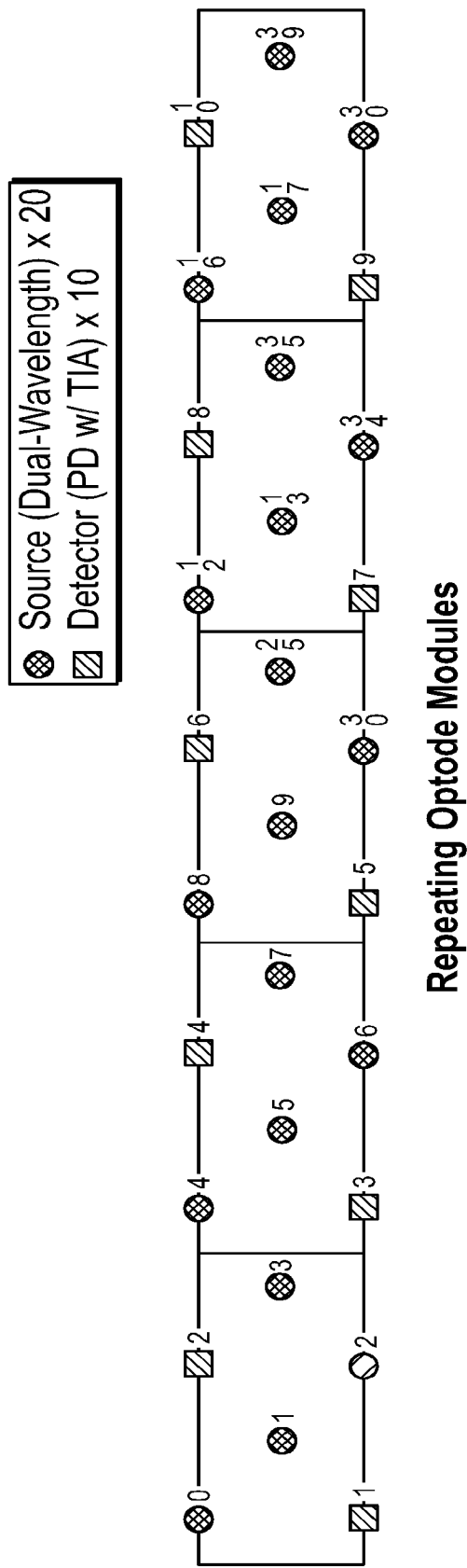

FIG. 10B depicts an illustrative implementation showing a series of repeating optode modules, consistent with various exemplary aspects of one or more implementations of the disclosed technology. Referring to FIG. 10B, a pattern of repeating optode modules is shown. Here, for example, such a pattern or component array may be configured to provide coverage/detection of a brain motor cortex area of a user when worn as part of a headset, headband, or other mode of mounting the pattern or array to a user's head. Further, additional modules may also readily and easily be added above and below to increase or extend coverage even further, as desired or needed in certain implementations. Although the example of 10B shows a linear array, optodes may be arranged in a variety of configurations to ensure that any and all desired regions of a user's brain can be evaluated for neural activity and/or activity patterns.

According to some example embodiments, herein, each optode module may include, utilize and/or involve an optode configuration, including but not limited to the innovative optode configurations set forth herein. Further, as shown in implementations herein, such optode modules include one or more central/centralized sources in conjunction with various other features, as opposed to other source-detector configuration(s). Among other things, by using an additional source (e.g., light or laser source, such as LED, etc.) in the center, the number of detection channels and the range of measurement depths increases. Here, for example, such implementations may create a variety of source-detector separation distances (e.g., such as three, in certain implementations, for example, 21, 30, 47 mm), which correspond to that quantity of (e.g., three) measurement depths. According to implementations herein, the 'short' channels (e.g., 21 mm in this illustrative embodiment) may be utilized to increase the signal-to-ratio of the other channels by removing non-neuronal physiological signals. For example, by setting a channel distance at 21 mm or thereabouts, the light only reaches the depth of the human skull and does not reach the brain tissue itself. In this example of signal differentiation, the signals from these 21 mm channels can then be subtracted from the signals of the other channels to remove the noise that arises from light interactions associated with the skull tissue. Further, some embodiments may have a medium channel of 30 mm and a long channel of 47 mm. Finally, it should be understood that such specific channel lengths are exemplary and other channel lengths and ranges fall within the ambit of the innovative technology disclosed. For example, the first channel may be a short channel of 19-23 mm, the second channel may be a medium channel of 28-32 mm, and the third channel may be a long channel of 45-49 mm. Further, the first or short channels may be 20-22 mm, the second or medium channels may be 29-31 mm, and the third or long channel may be 46-48 mm, in some embodiments.

Figure 10C:
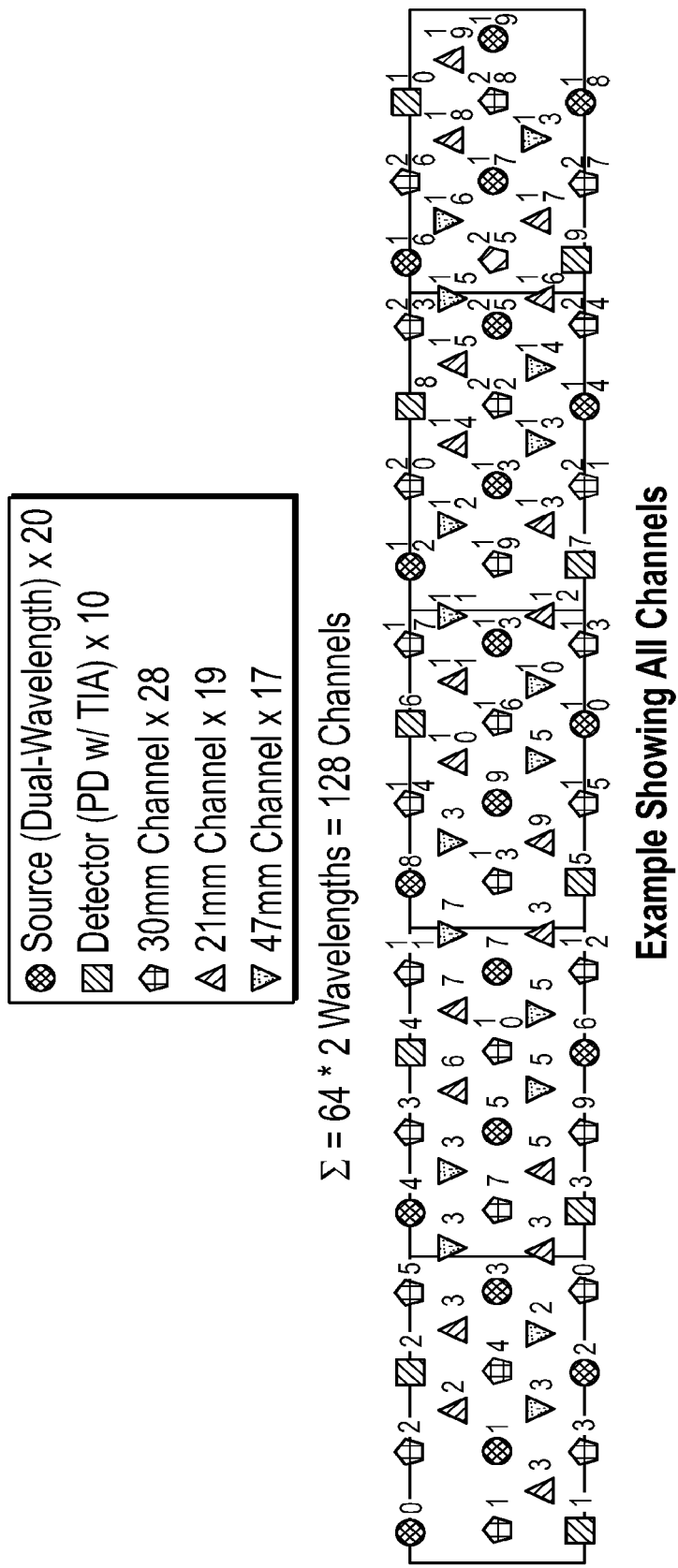

The exemplary implementations of FIGS. 10B and 10C also illustrate embodiments wherein the overall brain-computer interface device has 20 optical sources and 10 optical detectors. However, other embodiments may contain different quantities of such components. For example, such BCI devices can include 12-28 of the optical sources and 6-14 of the optical detectors, or, in certain embodiments, 16-24 of the optical sources and 8-12 of the optical detectors.

FIG. 10C depicts an exemplary embodiment showing a set of optode components and their configuration, illustrating a full set of possible channel locations available in one exemplary implementation. Further, in some embodiments such as the one illustrated in FIG. 10C, one or more of the optodes may also be configured to transceive at two (2) wavelengths, such as 735 nm and 850 nm. Additionally, according to some implementations, such embodiments may utilize a master sample rate (e.g., when using USB connection) of approximately 250 Hz, and utilize a channel sample rate (i.e., given by the master sample rate divided by the number of sources), which may, for example, by 6 Hz in certain exemplary instances.

Various implementations herein may also utilize various forms of connectivity to increase performance, such as sampling rate, according to one or more example embodiments. According to some implementations, for example, the disclosed technology may be constructed to include an inbuilt WiFi module, which enables an increase in the master sample rate to over 1 kHz, therefore increasing channel sample rate when leveraging all of the sources to at least 25 Hz.

Figure 11A:
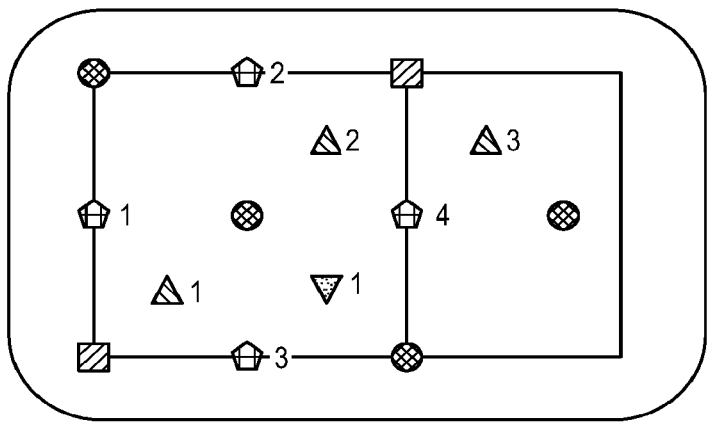
FIGS. 11A-11C depicts various other illustrative implementations regarding optode modules, consistent with various exemplary aspects of one or more implementations of the disclosed technology.
Figure 11B:
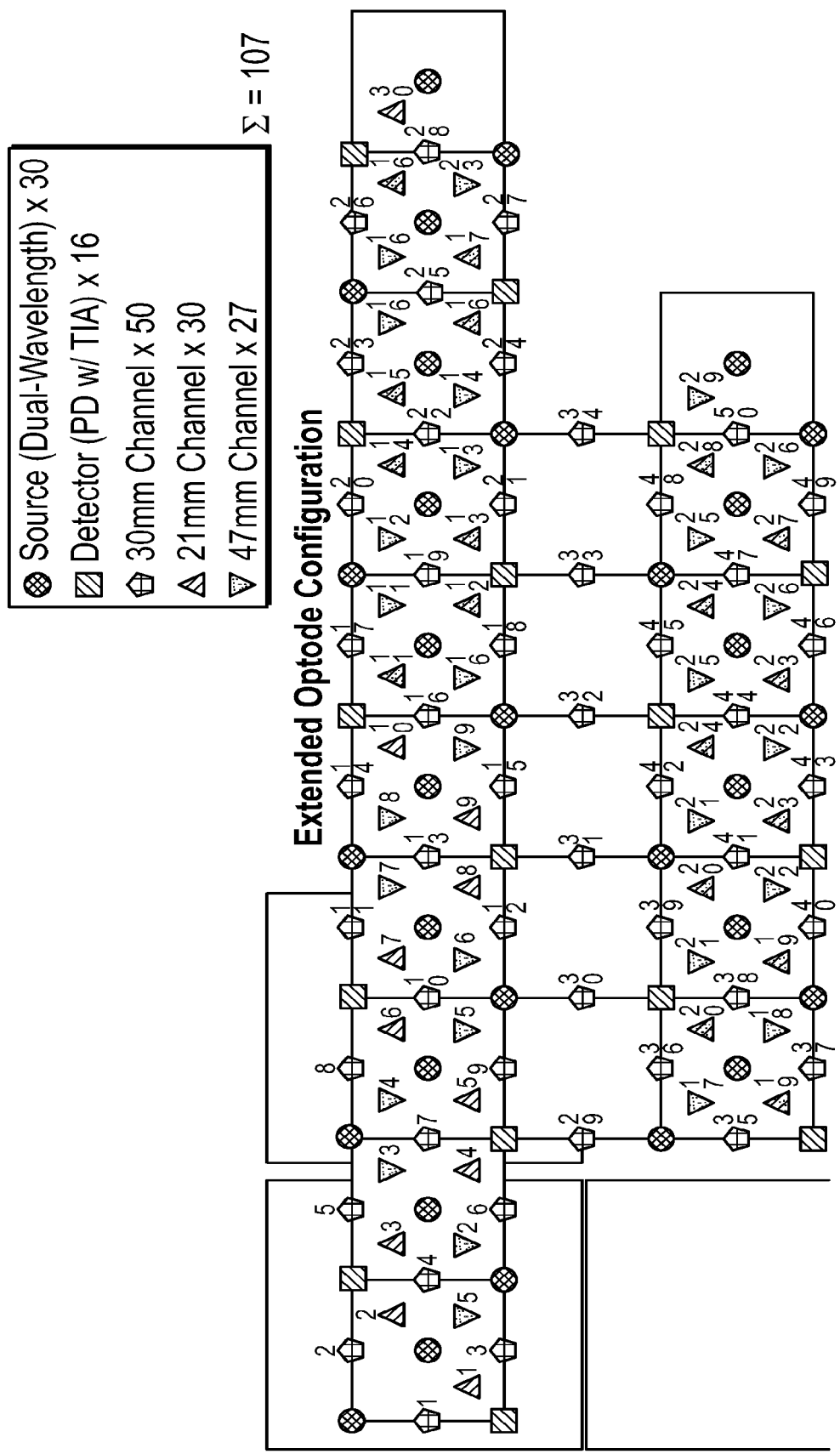
Figure 11C:
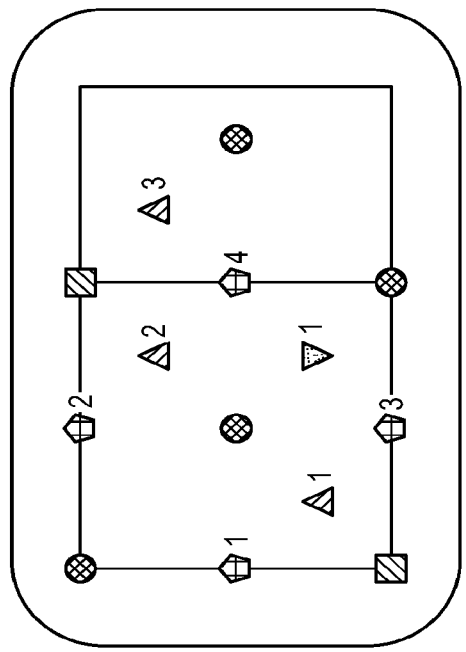

FIGS. 11A-11C depicts various other illustrative implementations regarding optode modules, consistent with various exemplary aspects of one or more implementations of the disclosed technology. Further, the embodiments of FIG. 11A shows a single optode module including four sources and two detectors, as well as possible channel locations. FIG. 11B illustrates an array of optode modules wherein some of the optode modules are in both series and parallel arrangement(s) with each other. The example module of FIG. 11B includes 30 optical sources, 16 optical detectors, 30 first or short channels, 50 second or medium channels, and 27 third or long channels. Of note, the individual optode modules in the array are arranged in two physical dimensions. This two-dimensional array can then be mapped on to the curved surface of a headband, headset, or other means of mounting the array to a user's head.

However, other embodiments may contain different quantities of such components. For example, BCI devices may include 26-34 of the optical sources and 12-20 of the optical detectors, or, in certain embodiments, 28-32 of the optical sources and 14-18 of the optical detectors.

Similarly, other embodiments may include 26-34 of the first or short channel, 44-56 of the second or medium channel, and 23-31 of the third or long channel, and/or they may include 28-32 of the first or short channel, 47-53 of the second or medium channel, and 25-29 of the third or long channel.

However, other embodiments may contain different quantities of such components. For example, BCI devices may include 28-36 of the optical sources and 12-20 of the optical detectors, or, in certain embodiments, 30-34 of the optical sources and 14-18 of the optical detectors.

Brain Computer Interface (BCI)+VR/XR with Eye Tracking, EEG and Other Features

Figure 12A:
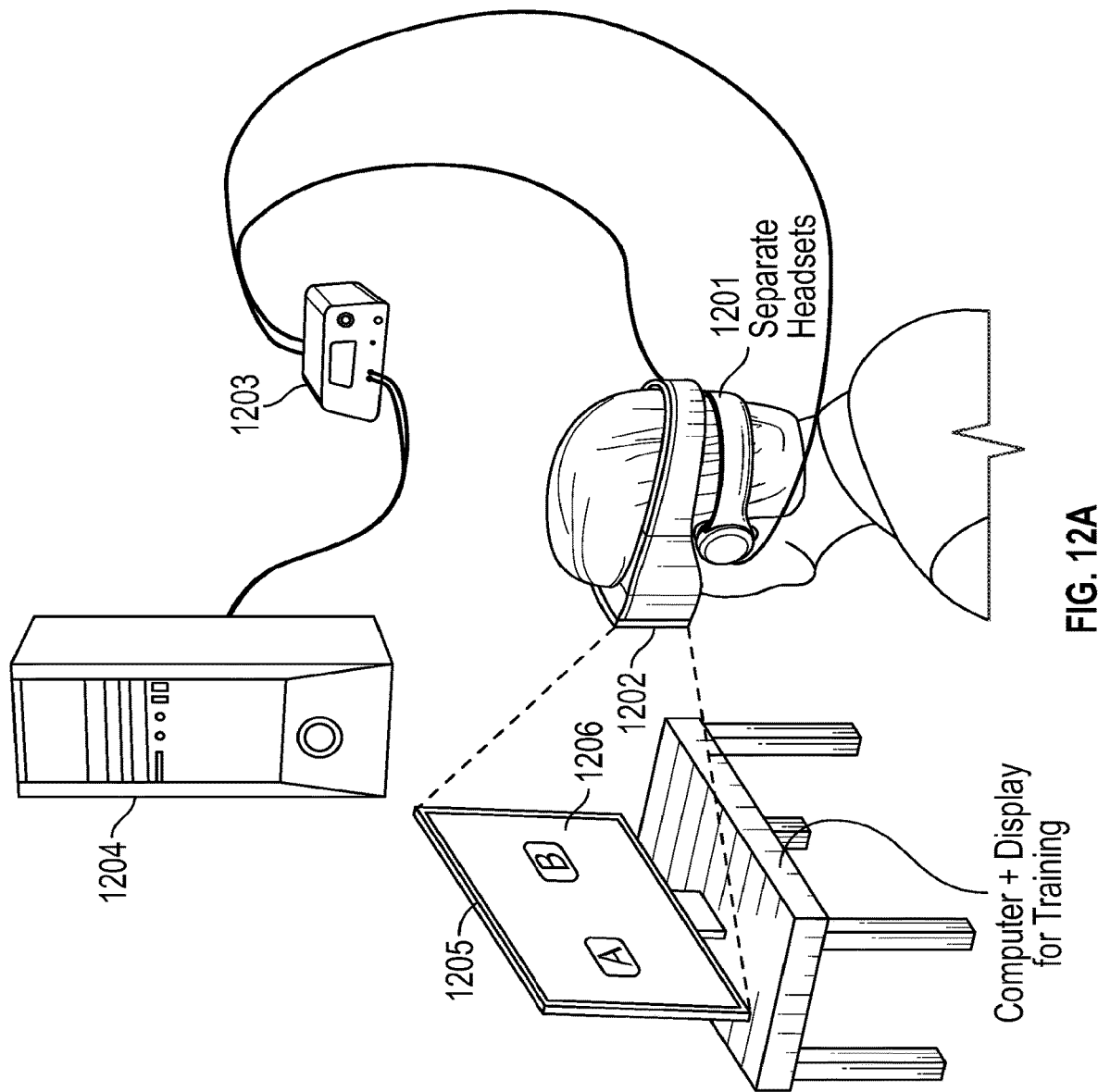
FIGS. 12A-12B depict two illustrative implementations including components associated with the combined VR and eye tracking hardware and EEG measuring BCI hardware, consistent with various exemplary aspects of one or more implementations of the disclosed technology.
Figure 12B:
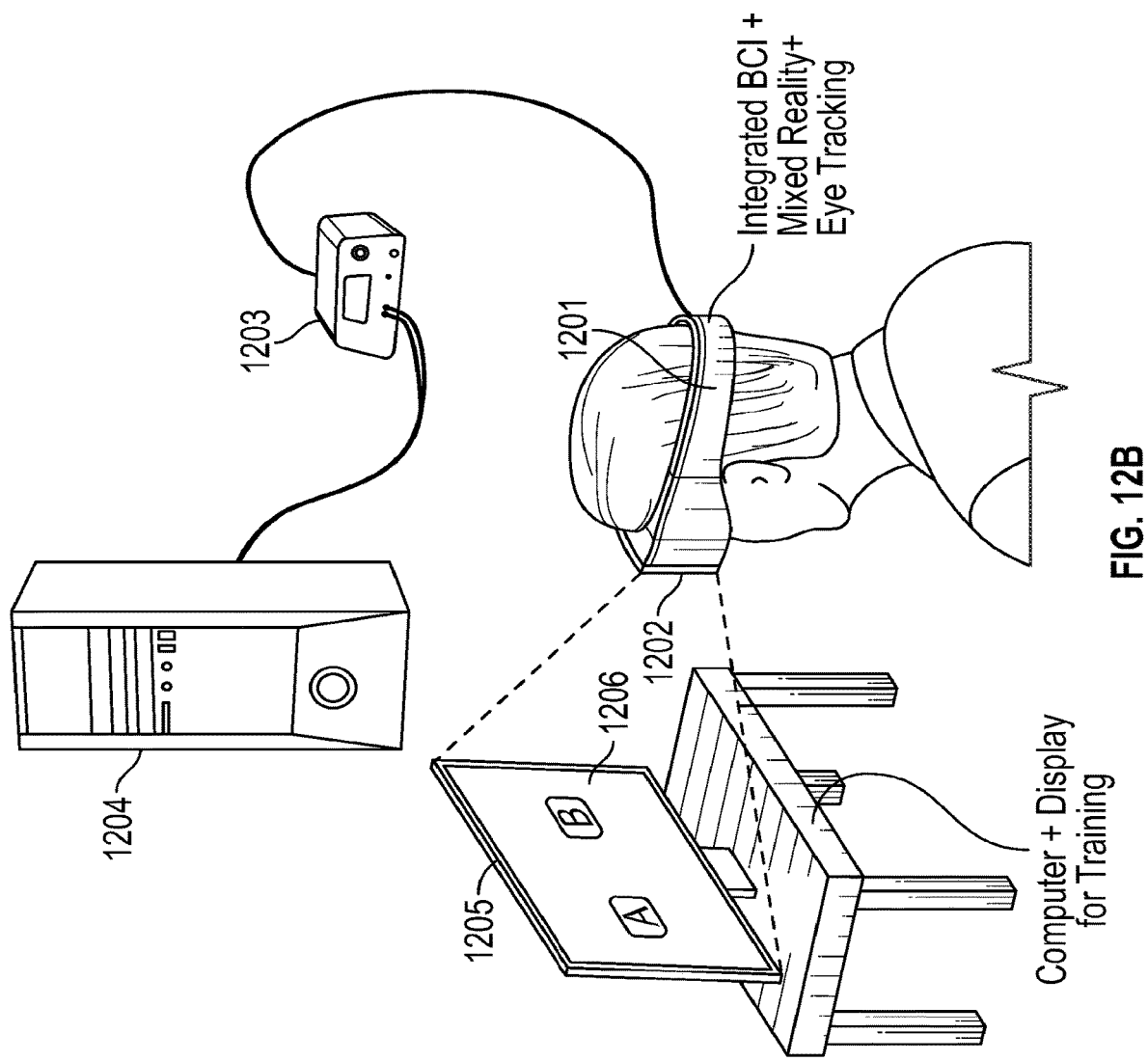

FIGS. 12A-12B depict two illustrative implementations including components associated with the combined VR (Virtual Reality) or XR (Extended Reality) as well as eye tracking hardware and EEG measuring BCI hardware, consistent with various exemplary aspects of one or more implementations of the disclosed technology. Herein, while the term VR headset 1202 is used in numerous instances for the sake of convenience, it should be understood that this term can refer to VR headsets, XR headsets, augmented reality headsets, glasses, headbands, and the like. In one illustrative embodiment, shown in FIG. 12A, the BCI and VR headset containing eye tracking hardware and software components are implemented as two separate components, such as two separate headsets. In another illustrative embodiment, shown in FIG. 12B, the BCI and VR headset containing eye tracking hardware and software components are contained within one combined headset. Other configurations and arrangements of such components may be utilized, e.g., in other embodiments. Consistent with the disclosed technology, the VR headset 1202 may further contain built in eye-tracking hardware and software components. Further, the VR headset 1202 may be arranged and configured to be capable of displaying a visual user interface, such as the exemplary visual user interface 1601 shown in FIG. 16. According to embodiments herein, the eye tracking hardware and software components of the VR headset may be utilized to measure a user's eye movement in response to the display of such visual user interface 1601. Further, the BCI 1201 may include or involve various optodes, electrodes, and/or other measurement instruments and/or functionality for the collection of EEG and other brain data, as described elsewhere herein.

In the illustrative embodiments shown in FIGS. 12A and 12B, such exemplary BCI 1201 and VR headset 1202 systems may also be connected to a computing component 1204 via variational autoencoder (VAE) 1203 (the function of which will be described in greater detail below), with the computing component 1204 operating and/or implementing software, which may be, e.g., in one embodiment, the Unity software system, but in other embodiments may include and/or involve any extended reality software system and which implements/displays an extended reality experience. In such embodiments, the BCI and VR headset components 1201 and 1202, connected to the computing component 1204, can be used to operate a virtual, augmented, or mixed reality experimental paradigm 1206. Here, for example, in some embodiments, the BCI 1201 and corresponding measurement instruments used with the BCI acquire EEG measurements while the VR headset 1202 with eye tracking hardware and software components simultaneously acquire eye tracking data. Further, according to the experimental paradigm, such features may be utilized in training and implementing the system. For example, in some embodiments when training the user to use the system, a VR game may be played where objects appear in a random position of the field of view. Here and otherwise, according to aspects of the disclosed technology, associated EEG signal data and eye position data may be detected and synchronously registered by the connected computing components 1204 of the system.

Figure 13A:
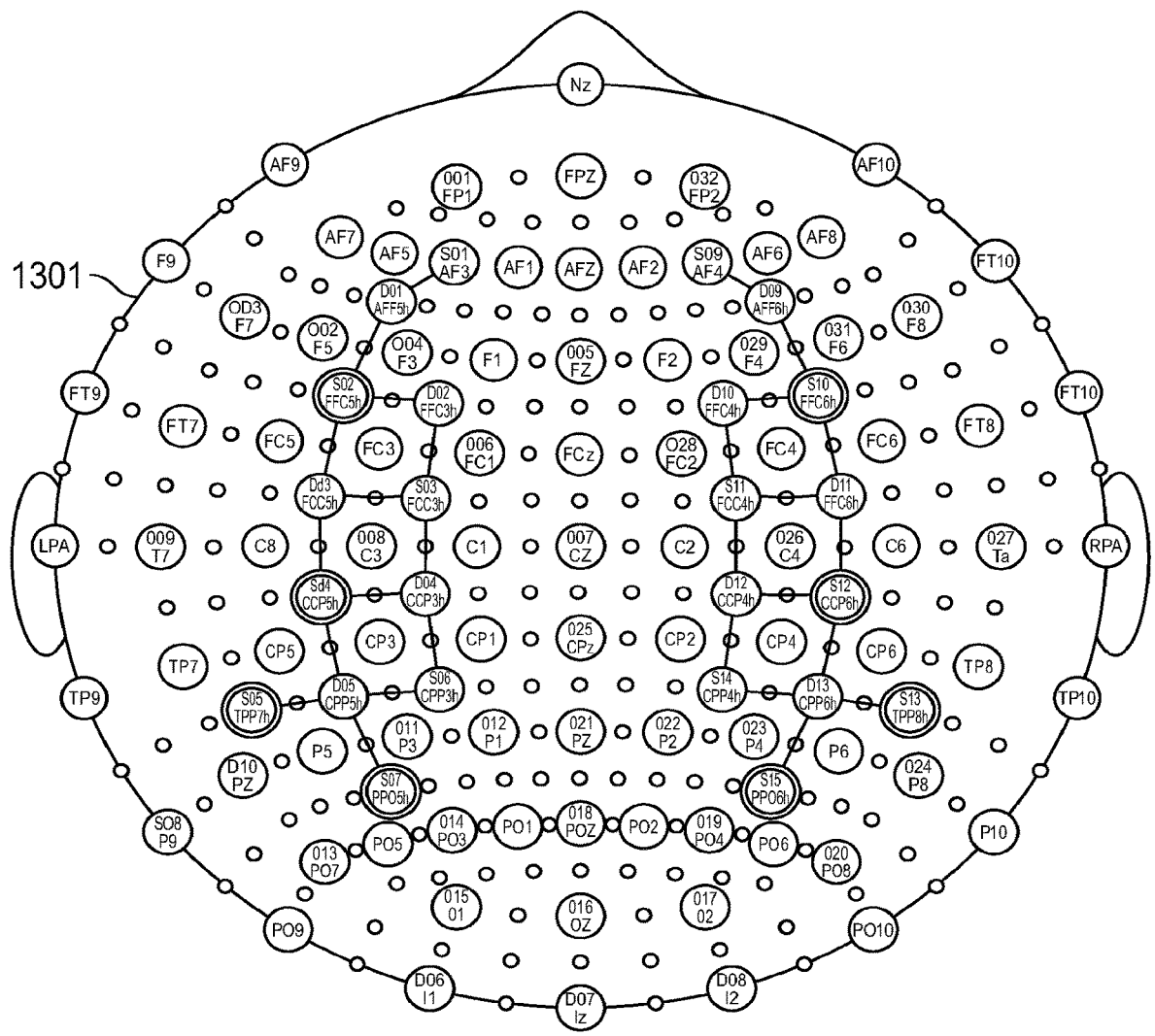
FIGS. 13A-13B depict two illustrative implementations including exemplary optode and electrode placement aspects associated with certain exemplary BCI hardware, consistent with various exemplary aspects of one or more implementations of the disclosed technology.
Figure 13B:
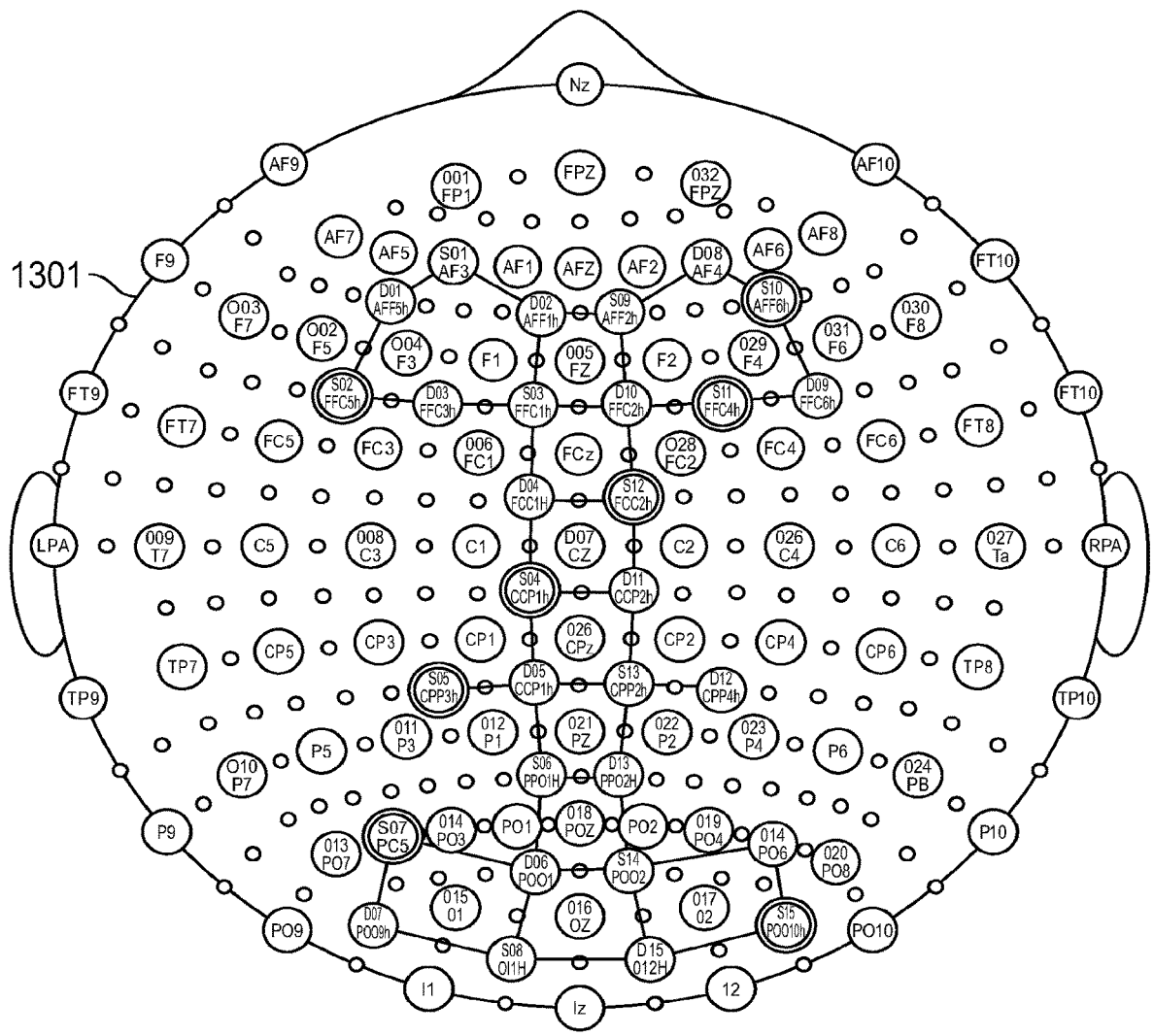

FIG. 13A depicts one illustrative electrode and optode arrangement or montage that may be utilized, e.g., in an exemplary implementation in which XR, VR, etc. eye-tracking information is involved, and such montage may include 36 channels, 68 optodes, 15 sources, 21 detectors, and 8 S.D. detectors. FIG. 13B depicts another illustrative electrode and optode arrangement or montage that may be utilized, e.g., in an exemplary implementation in which no XR, VR, etc. eye-tracking information is involved, and such montage may include 48 channels, 70 optodes, 15 sources, 23 detectors, and 8 S.D. detectors. Other quantities and ranges of such components may also be utilized, in various differing embodiments. Herein, while this one style or representation of the electrodes and optodes is depicted, other arrangements, configurations and/or illustrations of signal detection and acquisition hardware may also be used consistent with the inventions herein, such as those used by various organization affiliated with the study of the brain and/or sleep. According to other embodiments consistent with the disclosed technology, an electrode/optode arrangement may use some or all of the known 10/20 EEG system electrode/optode positioning, such as that of the 10/20 EEG placement described by the European Respiratory Society (ERS). Still other electrode and optode arrangements that provide suitable signals may also be utilized. The 10/20 EEG positioning is noted, as this is a standard arrangement used when recording brain data, particularly when recording using EEG devices. It is further noted that such 10/20 positioning, and other such electrode/optode placements, may be utilized in certain embodiments of the disclosed technology and inventions herein.

Referring to FIGS. 13A-13B, the illustrated montages of electrode and optode positions were specifically engineered to provide superior coverage/results regarding the brain activity most pertinent to aspects of the innovations herein, such as yielding accurate visual attention and saliency map determinations. According to various embodiments herein, for example, there is a denser clustering of sensors over some of the visual cortical areas of the brain including the primary visual (striate) cortex, the prestriate cortex and posterior parietal regions of the brain. Such montage positions may include optodes arranged to capture the optical data, as described above, and electrodes to capture specified EEG data, e.g., such as an array (ntrials×nchannels×nsamples) as explained further below. The exemplary sensor and detector locations of FIGS. 13A-13B are configured for utilization of EEG and Optical equipment for NIRS and fast optical signal processing. The exemplary sensor and detector montages of FIGS. 13A-13B are specific arrangements developed explicitly for this visual attention paradigm, with an emphasis on visual cortical areas. Additionally, these embodiments describe multimodal relationships, i.e., so they illustrate both EEG (electrodes) and optical detector locations for simultaneous measurements. Further, it is noted here that, while certain exemplary configurations of electrode and optode arrangements are shown in FIGS. 13A-13B, various other possible electrode and optode arrangements may be implemented to function in a same way to yield similar results. Among a variety of such alternative arrangements, for example, various electrodes (both dry and wet electrodes) and near-infrared optodes may be utilized in a regular arrangement purely over the visual cortex of the participant, removing any data acquired from other brain regions. As one further example of such alternative arrangements, systems and methods involving active channel selection may be utilized, whereby brain data is recorded in a standard arrangement such as 10/20 system EEG arrangement, and then the channels which best contribute to an accurate saliency map in training can be selected automatically via an algorithm, e.g., based on each channel's weighted contribution to the accurate parts of the saliency map.

Visual-attention-related information may be primarily captured from electrodes placed over the occipital and parieto-occipital regions, as these areas are closely associated with visual processing. Additionally, some areas of the parietal lobe are involved in directing attention and processing visual spatial information.

In some embodiments, the systems described herein may use various channels (e.g., EEG channels, or individual EEG electrodes for capturing brainwave activity) for visual attention-based information. In one embodiment, the systems described herein may use occipital areas associated with primary visual processing including any or all of (i) O1 and O2 which are traditional occipital electrodes, (ii) Oz which is centrally located over the occipital lobe, and/or (iii) Iz which is an inferior occipital electrode. Additionally or alternatively, the systems described herein may use parietal-occipital electrodes or channels, including POz, a parieto-occipital central electrode, and/or PO3, PO4, PO7, and PO8, parieto-occipital electrodes that provide coverage of the region where parietal and occipital lobes meet, crucial for visual processing and attention.

In one embodiment, the systems described herein may use electrodes in the parietal area, which is associated with visual spatial attention and integrating sensory information, including P3, P4, Pz, P1, P2, P5, and/or P6. In some embodiments, the systems described herein may use temporal electrodes or channels that can capture activity related to higher-level visual processing and attention, especially when visual stimuli have a strong semantic or emotional component, such as T5 (or P7) and/or T6 (or P8).

The systems described herein may use various channels to derive motor intention information. The process of voluntary movement begins in the prefrontal and parietal areas, where the intention to move is generated. This intention is then transmitted to the primary motor cortex, which is responsible for planning and executing actions. The primary motor cortex receives input from other areas of the brain, such as the somatosensory cortex, which provides information about the position and movement of the body's limbs and joints. This information, combined with the intention to move, generates signals that coordinate the activity of motor neurons.

In one embodiment, the systems described herein may use channels from those brain regions that include prefrontal areas, such as Fp1 and Fp2 located on the forehead and/or AF3, AF4, AF7, and AF8 that are additional frontal-polar electrodes that provide more detailed coverage of the prefrontal areas. Channels used for motor information in the parietal regions may include (i) P3 and P4, traditional parietal electrodes, (ii) Pz, centrally located over the parietal lobe, and/or (iii) P1, P2, P5, P6, PO3, PO4, PO7, and PO8, additional parietal and parieto-occipital electrodes that provide more detailed coverage of the parietal areas. The systems described herein may use various electrodes positioned over the primary motor cortex areas, including (i) C3 and C4, located over the primary motor cortex, (ii) Cz, centrally located over the primary motor cortex, and/or (iii) C1, C2, C5, and C6, additional central electrodes that provide more detailed coverage of the primary motor cortex areas.

Returning to the examples of FIGS. 12A and 12B, the VR headset can be capable of generating a stimulus presentation 1205 to create trials for data collection utilizing both the BCI and VR headsets. Such a stimulus presentation 1205 may include, but is not limited to, the presentation of visual stimulus in the form of flashes of light and alternating light and colors across the VR headset 1206. The EEG signal data captured by the BCI 1201 and the visual data captured by the VR headset 1202 are both captured and synchronously registered in specified windows of time surrounding each visual stimulus event produced by the VR headset 1202. In one embodiment, the window of data collection and registration occurs beginning one second before the visual stimulus event and extending three seconds after the disappearance of the visual stimulus. In other embodiments, the window for data capturing may be at other intervals to acquire more or less data surrounding a visual event.

According to some embodiments, the raw EEG data may be captured and configured as an array formatted to include the number of trials ($N_1$) by the number of channels ($N_2$) by the number of samples ($N_3$). Further, in one exemplary implementation, the images of data may then be encoded into data streams from the BCI 1201 and VR headset 1202 eye tracking hardware and software components to the computing component 1204 using a variational autoencoder (VAE) 1203. In embodiments here, a variational autoencoder 1203 may be utilized because there is not always a one-to-one relationship between brain activity and the user's attention in a visual saliency map, in other words there may occur a different brain activation time for each event but can correspond to the same task. Using a variational autoencoder 1203 allows for estimating the distribution (characterized by the mean and the standard deviation) of the latent space 1407 (illustrated in and described in connection with FIGS. 14A and 14B), meaning the apparatus can be used to study the relationship between the distribution of brain activations rather than just a one-to-one relationship between the latent vectors. Each sample of raw brain data is converted to images in the format as [n trials×n down×h'w].

Figure 14A:
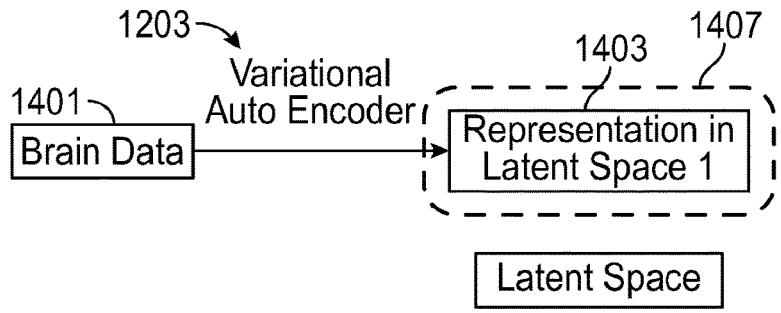
FIGS. 14A-14B depict exemplary process flows associated with processing brain data and eye tracking data and converting the data to compressed images in latent space, consistent with various exemplary aspects of one or more implementations of the disclosed technology.
Figure 14B:
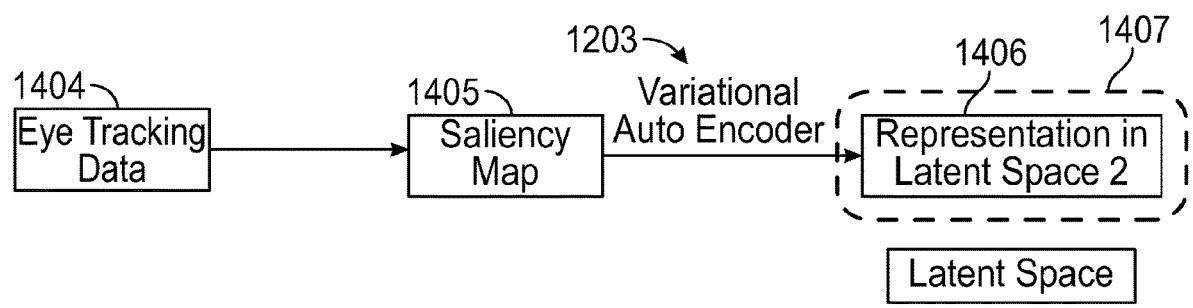

FIGS. 14A-14B depict exemplary process flows associated with processing brain data and eye tracking data and converting the data to compressed images in the latent space, consistent with various exemplary aspects of one or more implementations of the disclosed technology. Referring first to the process map in FIG. 14A, the variational autoencoder 1203 encodes both the BCI data 1401 and the VR eye tracking data 1404 from the BCI 1201 user interface and the VR headset 1202 user interface to the computing component 1204 in latent space 1407. In some embodiments, brain data 1401 can be translated and converted into eye tracking data and used as all or part of eye tracking data 1404. Latent space 1407 is a theoretical representation of the process of transforming and compressing the raw data (from the BCI 1401, and from the VR headset 1404) output from the BCI 1201 and VR headset 1202, to the images in a specified format, or the Representations in the Latent Space 1 and 2 (1403 and 1406 respectively), which in combination form all or a part of latent space 1407. In other embodiments, the images generated may be in a format other than the format specified above, where such other data image formats are equivalent, e.g., function in a same way and/or achieve similar result as the formats specified above. Here, for example, with recent demands of deep learning applications, synthetic data have the potential to become a vital component in the training pipeline. As a result, a multitude of image synthesis methods now exist which can be implemented with or involved in particular brain-computer interfacing contexts of the present inventions. Further, various of these image synthesis methods have not been applied to brain data previously, though due, e.g., to the capability to transform the data into conventional computational forms such as matrices and vectors in some cases, such image synthesis methods are applicable in the instant brain-computer interfacing contexts and would represent novel usage.

Similarly, while the present embodiment specifies using a variational autoencoder 1203 to encode the data streams, 1401 and 1404, other encoders or comparable hardware and/or software can be used to encode the data received from the BCI 1201 and VR headset 1202 eye tracking hardware and software components. Among other options, for example, in the place of a variational autoencoder, a generative adversarial network (GAN) may be utilized to synthesize image data directly from the eye-tracking data and then use another GAN to synthesize the brain data derived saliency map consistent with the inventions described herein. In still other embodiments, a diffusion method and/or a transformer may also be utilized.

In addition, there are a number of data augmentation techniques which can subsequently be applied to the synthetic image data to enlarge the dataset and potentially improve the accuracy of the discriminator, including but not limited to flips, translations, scale increases or decreases, rotations, crops, addition of Gaussian noise, and use of conditional GANs to alter the style of the generated image.

In still other implementations, brain data other than EEG may be utilized consistent with systems and methods of the disclosed technology, e.g., to provide similar or comparable functionality and/or similar results. Examples of other brain data that may be utilized, here, include NIRS, FOS, and combined EEG.

In some embodiments EEG brain data images 1501 are generated from the raw brain data 1401 features obtained (as encoded and compressed by the variational autoencoder 1203, in some embodiments), based on the spatial location of the features, optodes, or electrodes on the user's head. Consistent with the innovations herein, autoencoding of a saliency map from the brain data may be achieved, inter alia, via a four-part process:

Part 1. Constructing Images from Raw Brain Data Via Spatial Location of Features on the User's Head According to aspects of the disclosed technology, generation of brain data images may be accomplished by creating an array of data from multiple trials (e.g., via creation of a visual or other stimulus 1206 by the VR headset 1202, shown in FIGS. 12A-12B), then organizing each trial data set by electrode number, and by time. The trial data sets may be organized in other ways, as well, consistent with the innovations herein. According to certain systems and methods herein, the data may be additionally processed to obtain the desired/pertinent signals. In some embodiments, for example, a low-pass filter and/or down sampling can be applied to the data, such as through the variational autoencoder and/or other computing components, to extract just the pertinent signals, while excluding the artifacts or unwanted data. Further, the data may be preprocessed using the computing components to remove the remaining noise and artifacts, or unwanted data. The data may then be represented on a two-dimensional map, such as via utilization of an azimuthal projection calculation. Next, in some implementations, the data may be represented as a continuous stream of data through bicubic interpolation, and this process may be repeated for all data samples collected by trial and separated by electrode location. In accordance with such aspects, the data stream created through bicubic interpolation and subsequent projection onto a two-dimensional map through azimuthal projection is then concatenated from each sample to produce an image with the number of channels corresponding to the number of temporal samples after down-sampling the signals. Finally, a process or step of normalizing the data may then be performed, e.g., after such image generation and down-sampling is performed.

Note that the above-described features represent only one exemplary methodology regarding taking and processing the raw data from the BCI 1401 and representing such data in a two-dimensional map. Other methods may be used to represent the raw data in a two-dimensional map and may be utilized to achieve the desired result(s), here, consistent with the disclosed technology. Among other things, e.g., calculations other than a bicubic interpolation may be used to interpolate the data, projections other than an azimuth projection may be used to map the signal data, and/or filtering and down sampling are ways to exclude unwanted data though are not necessary to achieve the result(s) or they may be achieved in a consonant way.

In certain embodiments herein, a random signal following a Gaussian distribution of zero mean or average and a standard deviation of 0.25 can be added to the filtering and image creation model to increase the model's stability and to better filter between noise and EEG signals. Further, according to some implementations, the use of an image format leads to better results when using convolutional networks than when using a simple array representation of the brain data, but the use of simple array representations of brain data may still be utilized, in various instances, to achieve desired results consistent with the innovations herein.

Part 2. Processing EEG Images (e.g., Through a VAE) to Represent in Latent Space As can be seen, in part, in FIG. 14B, a process of utilizing or involving a variational autoencoder 1203 to encode and filter eye tracking data 1404 may be performed to create a saliency map 1405 represented in the latent space 1407 derived from the eye-tracking data 1404. According to implementations, here, the raw eye-tracking data 1404 may first be converted to a saliency map 1405 of the user's attention using existing methods (e.g., while watching something, one can extract saliency features representing the degree of attention and average position of the center of interest in the video). Then, a variational autoencoder such as variational autoencoder 1203 may be applied to recreate the saliency images or map representations of the images 1406 in latent space 1407. In some examples, using a raw eye tracker in some instances, the systems and methods described herein can create a visual saliency map representing the area of attention in an image of one channel with values between 0 and 1 representing the degree of visual attention on specific pixels and their neighbors. As such, the data and corresponding value between 0 and 1 can also be considered as a probability for a given pixel to be watched or not. Accordingly, visual saliency images 1405 as representations 1406 in the latent space 1407 are thus generated.

Part 3. Generation of Visual Saliency Images

In some embodiments, VR eye tracking and EEG data and resulting two-dimensional maps may be generated and/or recorded simultaneously. Further, discrete VR eye tracking measurements may be projected on two-dimensional images (e.g., one per trial). According to certain aspects, accuracy may be taken into account using circles of radius proportional to error rate. Further, in some instances, Gaussian filtering may be applied with kernel size corresponding to the eye-tracker field of view, to improve output/results.

Part 4. Representing the Images in Lower Sub Space

Once the saliency images have been generated, the images may be represented in a lower sub space. Here, for example, in some embodiments, a variational autoencoder may be trained to represent the images in a lower sub space. In one illustrative embodiment, for example, a ResNet architecture may be utilized, though in other embodiments similar software and/or other programming may be used. Here, e.g., in this illustrative implementation, for the encoding section, four (4) stacks of ResNet may be used, each with 3 conversion layers and batch norm separated by a max pooling operation, though other quantities of such elements may be utilized in other embodiments. Further, in such illustrative implementations, in a decoding section, the same architecture may be utilized though with an up-sampling layer instead of a max-pooling operation. Moreover, regardless of the exact architecture, an objective of such autoencoding saliency map network is to recreate an image as close as possible to the original saliency map with a representation in shorter latent space. Additionally, in some embodiments, the latent space can be continuous, without favoring one dimension over another. Finally, in one or more further/optional embodiments, data augmentation techniques may be implemented or applied to avoid overfitting of the variational autoencoder.

Figure 15:
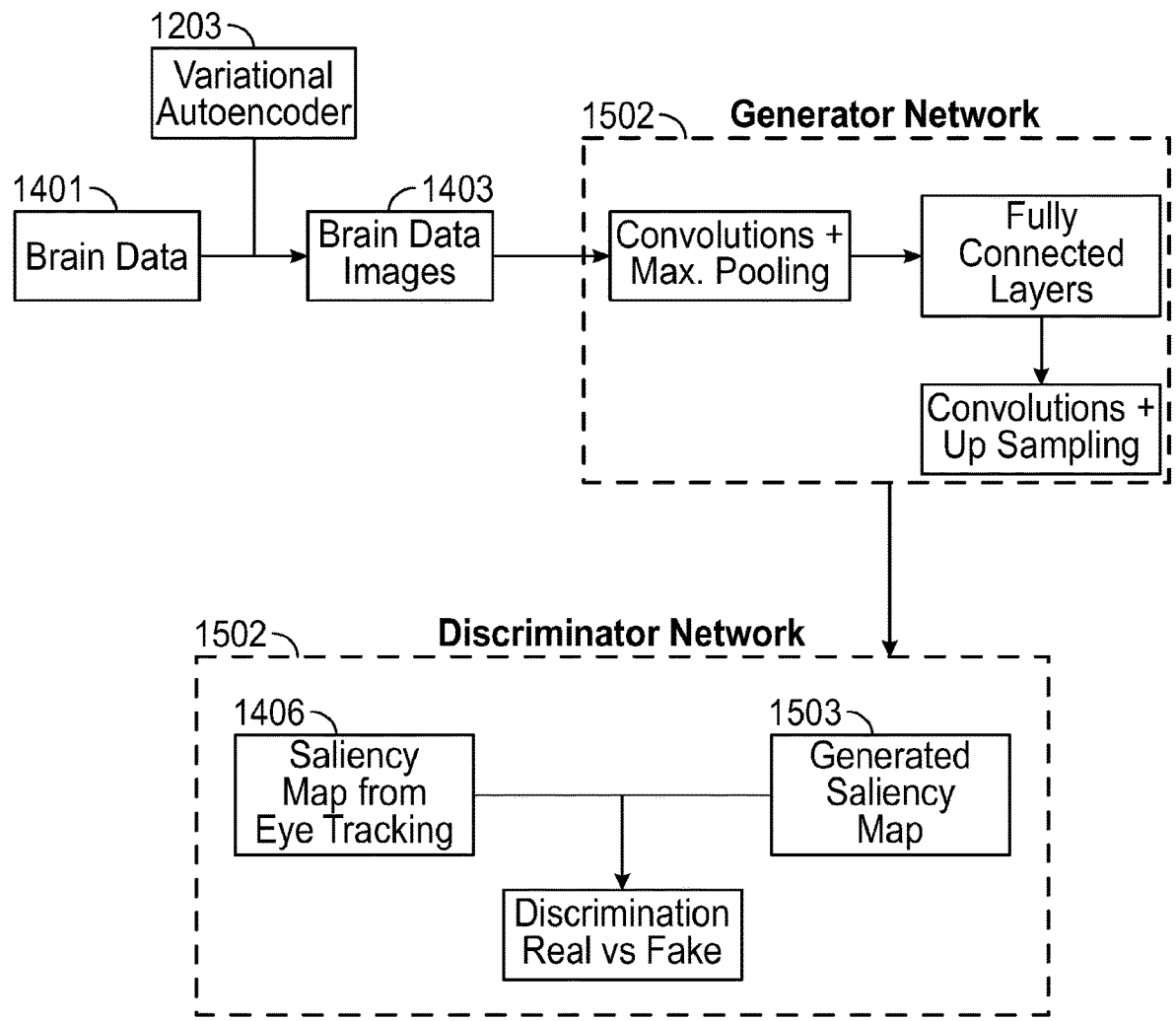
FIG. 15 depicts an exemplary flow diagram associated with processing compressed images from latent space as well as creation of a generator/discriminator network for comparison of EEG generated versus eye tracking actual visual saliency maps, consistent with various exemplary aspects of one or more implementations of the disclosed technology.

FIG. 15 depicts an exemplary flow diagram associated with processing compressed images from the latent space as well as creation of a generator/discriminator network for comparison of EEG generated versus eye tracking actual visual saliency maps, consistent with various exemplary aspects of one or more implementations of the disclosed technology. As shown in part via the process map of FIG. 15, in some embodiments, e.g., after the generation of both the EEG two-dimensional map (illustrated as brain data images 1403) and the eye tracking data visual saliency map 1406, a generator/discriminator adversarial network (GAN) 1502 for producing the generated saliency map 1503 may be implemented.

FIG. 15 also illustrates an exemplary GAN (illustrated as generator network 1502), which can combine the EEG/brain data latent space with the saliency latent space derived from two VAEs, e.g., such as those described above in connection with FIGS. 14A and 14B. In some examples, a goal is to map the 2 distributions (e.g., the map from the eye tracking and the map from the EEG signals in the illustrated example). Consistent with certain embodiments, an aim is to create a model permitting the estimation of a saliency map from EEG without considering a 1:1 correspondence between modalities.

Referring to the example embodiment of FIG. 15, such a GAN implementation may achieve the desired objective(s) via use of various aspects and features. For example, implementations herein may utilize a generator or generator network 1502 to recreate the image latent representation from EEG latent representation. In the example generator model shown and described, here, the generator may be created/implemented by concatenating the two parts of the VAE and linking them with fully connected layers, e.g., CNN (convolutional neural network) layers, etc. Further, a discriminator or discriminator network 1504 may be utilized to distinguish the images derived from the generator (e.g., in this illustration, as generated from the EEG representation which was in turn generated by the encoding and decoding part of the VAE) and those that are just derived from the eye tracking VAE. According to some embodiments, noise following a normal-centered distribution may be concatenated to the latent vector at the center of the generator. Overall, in the example shown in FIG. 15, the generator network 1502 may perform the concatenation of the encoding part of the EEG VAE and decoding part of saliency VAE through a generator composed of fully connected layers.

Additionally, as shown in FIG. 15, a discriminator network 1504 is then placed at the end of the model. Here, for example, discriminator network 1504 may then process the output(s) of the generator network 1502 and discern whether the saliency maps are derived from the model (synthetic) or from the real-time eye-tracking recordation.

Importantly, it is also noted that other methods besides adversarial methods or processing (i.e., other than GAN, etc.) can be utilized in order to produce a saliency map from brain data. Examples of such other methods include, though are not limited to, transformer architectures and/or diffusion models (e.g., denoising diffusion models/score-based generative models, etc.) and other implementations that work in this context by adding Gaussian noise to the eye-tracking derived saliency map (the input data), repeatedly, and then performing learning to get the original data back by reversing the process of adding the Gaussian noise.

Figure 16:
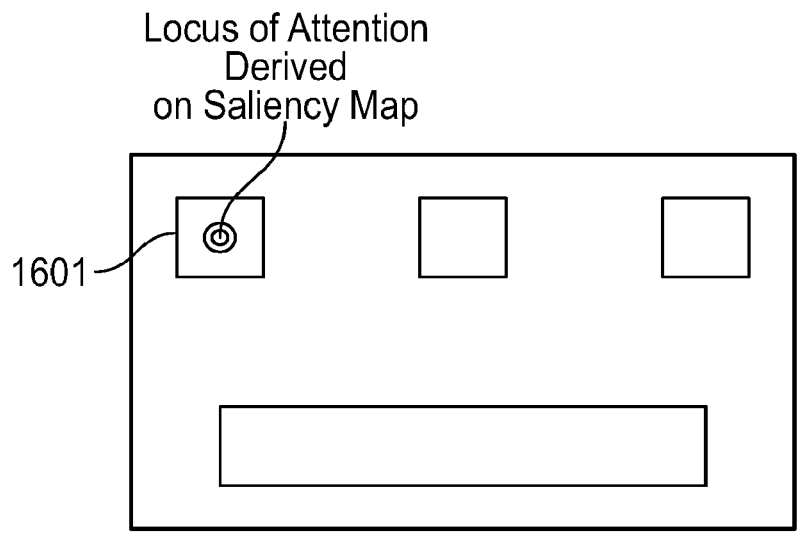
FIG. 16 depicts an exemplary user interface generated by a VR headset, consistent with various exemplary aspects of one or more implementations of the disclosed technology.

FIG. 16 depicts an exemplary user interface generated by a VR headset, consistent with various exemplary aspects of one or more implementations of the disclosed technology. Referring to FIG. 16, an exemplary user interface is depicted, e.g., as generated by the system/component(s) herein such as a VR or other headset, consistent with various exemplary aspects of one or more implementations of the disclosed technology. As shown in FIG. 16, an example user interface 1601, which may be two-dimensional (2D) or three-dimensional (3D) may be generated and employed to represent a 'heat spot' image indicating the locus of attention of the user and therefore which element the user would like to select in the environment.

Figure 17:
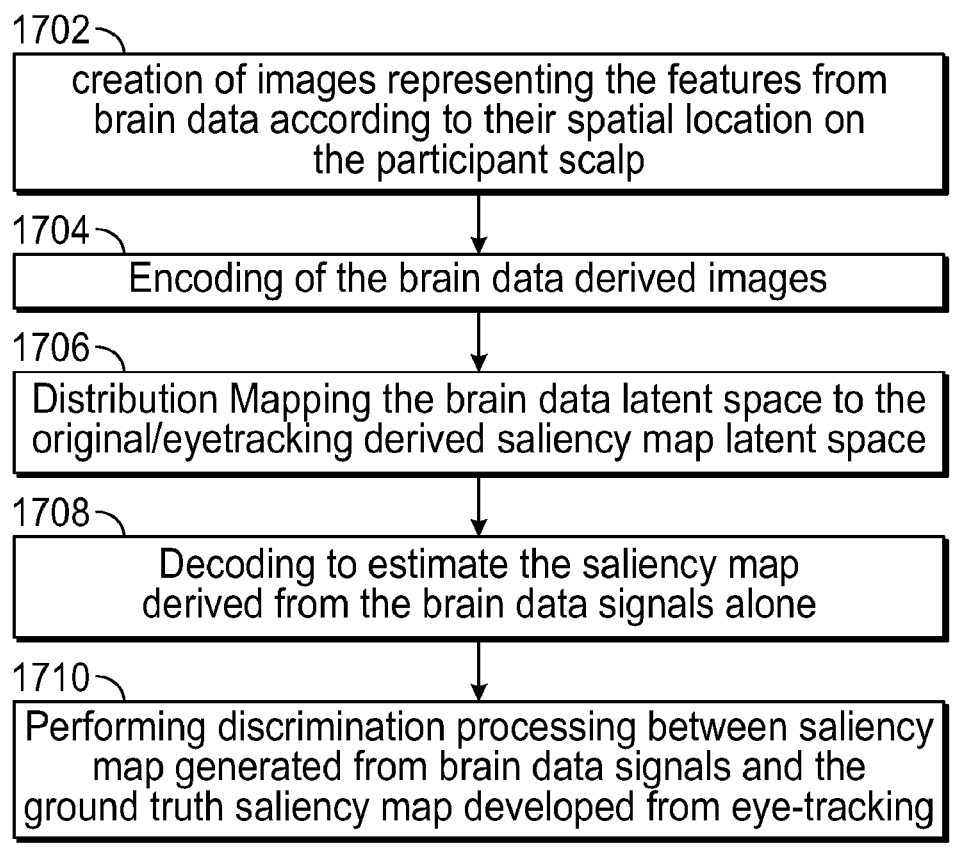
FIG. 17 depicts an illustrative flow diagram detailing one exemplary process of using a VR (and/or other) headset in combination with a BCI to create and compare a ground truth visual saliency map with a BCI-EEG generated visual saliency map, consistent with various exemplary aspects of one or more implementations of the disclosed technology.

FIG. 17 depicts an illustrative flow diagram detailing one exemplary process of using a VR (and/or other) headset in combination with a BCI to create and compare a ground truth visual saliency map (e.g., developed from eye tracking) with a BCI-EEG generated visual saliency map, i.e., to update the performance of the generator adversarial network, consistent with various exemplary aspects of one or more implementations of the disclosed technology. Referring to FIG. 17, an exemplary approach may be utilized to estimate visual attention of a user directly from EEG data taken from a BCI, while simultaneously recording data from VR headset eye tracking hardware and software components to create a visual saliency map to update and refine the EEG measurement data. An illustrative process utilized to estimate visual attention directly from brain data, may include steps such as: creating images representing the features from brain data according to their spatial location on the participant scalp, at 1702; encoding of the brain data derived images using, at 1704, which may be performed, e.g., via a variational autoencoder (example above) or similar equipment or components; performing distribution mapping of the brain data latent space to the original/ground truth/eye tracking derived saliency map latent space, at 1706; decoding the distribution map to estimate the saliency map derived from the brain data signals alone, at 1708; and performing discrimination processing between the saliency map generated from brain data signals and the ground truth saliency map (e.g., developed from eye-tracking), at 1710. Consistent with such process, a loss function may be derived, which is then used to update the performance of the generator network. Accordingly, such processing provides for more accurately estimating visual attention directly from the brain data, such as by more accurately mapping the user's locus of attention using EEG signals detected through the BCI alone. Further, in other embodiments, such processing and modeling may also be utilized for other estimations from brain data. By way of one example, a quantified map of a user's body movement may be derived from brain data, such as by first using a 3D body movement tracker or sensor, taking the place of the eye-tracker used in this visual attention context, and then generating an appropriate saliency map from the brain data associated with the brain activity derived from, for example, the user's premotor and motor cortices. Further, such a 'motor saliency map' may then be utilized, to, e.g., predict the imagined and intended movement of a user purely from the brain data recorded from the premotor cortex, in the absence of tracking the user's body movements directly with an external body tracker. In another such example, a quantified emotional state of a user may be derived, such as by first using a combination of signals derived from external signals such as eye movements, heart rate, body movement, sweat sensors, glucose sensors, etc., to derive a quantified map of a user's emotional state by weighting the various external signals according to a graph or scale of human emotions and the corresponding bodily signals. Based on this, an appropriate saliency map from brain data from a across the user's neocortex may then be generated via a similar method to that described in the visual attention context, by having the machine learning network learn to generate the equivalent saliency map from the brain data alone. This 'emotional saliency map' may then be utilized to predict a user's emotional state automatically using, e.g., the presently described brain-computer interface headwear or equivalent.

Visual Attention Tracking with Eye Tracking and Utilization of BCI+XR/VR/Etc. Saliency Mapping to Generate a Brain-Derived Selection (e.g., "Click")

1. Participant Wears a BCI Headgear with Eye Tracking and/or XR/VR/Etc. Headset

With regard to initial aspects of capturing and/or gathering various BCI and/or eye-tracking information from a user, the technology illustrated and described above in connection with FIG. 11A through FIG. 15 may be utilized in some embodiments, though various inventions herein are not limited thereto. Namely, it is noted that, in the context of the inventions disclosed here, various other types of technologies, such as differing BCI and/or eye-tracking devices and their associated signals, may also be utilized in implementations consistent with the presently-disclosed technology, such as the alternative examples of devices (e.g., BCI and/or eye-tracking devices, etc.) set forth herein.

a. Electrode/Optode Arrangement with the XR/VR/Etc. Headset

With regard to the electrode/optode arrangements, embodiments herein that involve capturing and/or gathering various BCI information from a user along with capture of eye-tracking information via use of an XR, VR, etc. headset may utilize the electrode/optode arrangement and related aspects set forth and described above in connection with FIG. 13A. Similarly, though, as above, it is noted that, in the context of these innovations, various other types of devices and technologies, such as differing BCI and/or eye-tracking devices and their associated signals, may also be utilized in such implementations, including the alternative examples of devices (e.g., BCI and/or eye-tracking devices, etc.) set forth herein.

b. Electrode/Optode Arrangement with No XR/VR/Etc. Headset

With regard to the electrode/optode arrangements initial aspects of capturing and/or gathering various BCI information from a user without any corresponding use of such XR, VR, etc. headset, the electrode/optode arrangement and related aspects set forth and described above in connection with FIG. 13B may be utilized. Further, as above, it is noted that, in the context of these innovations, various other types of devices and technologies, such as differing BCI devices and their associated signals, may also be utilized in such implementations, the alternative examples of devices (e.g., BCI, etc. devices) set forth herein.

Figure 18:
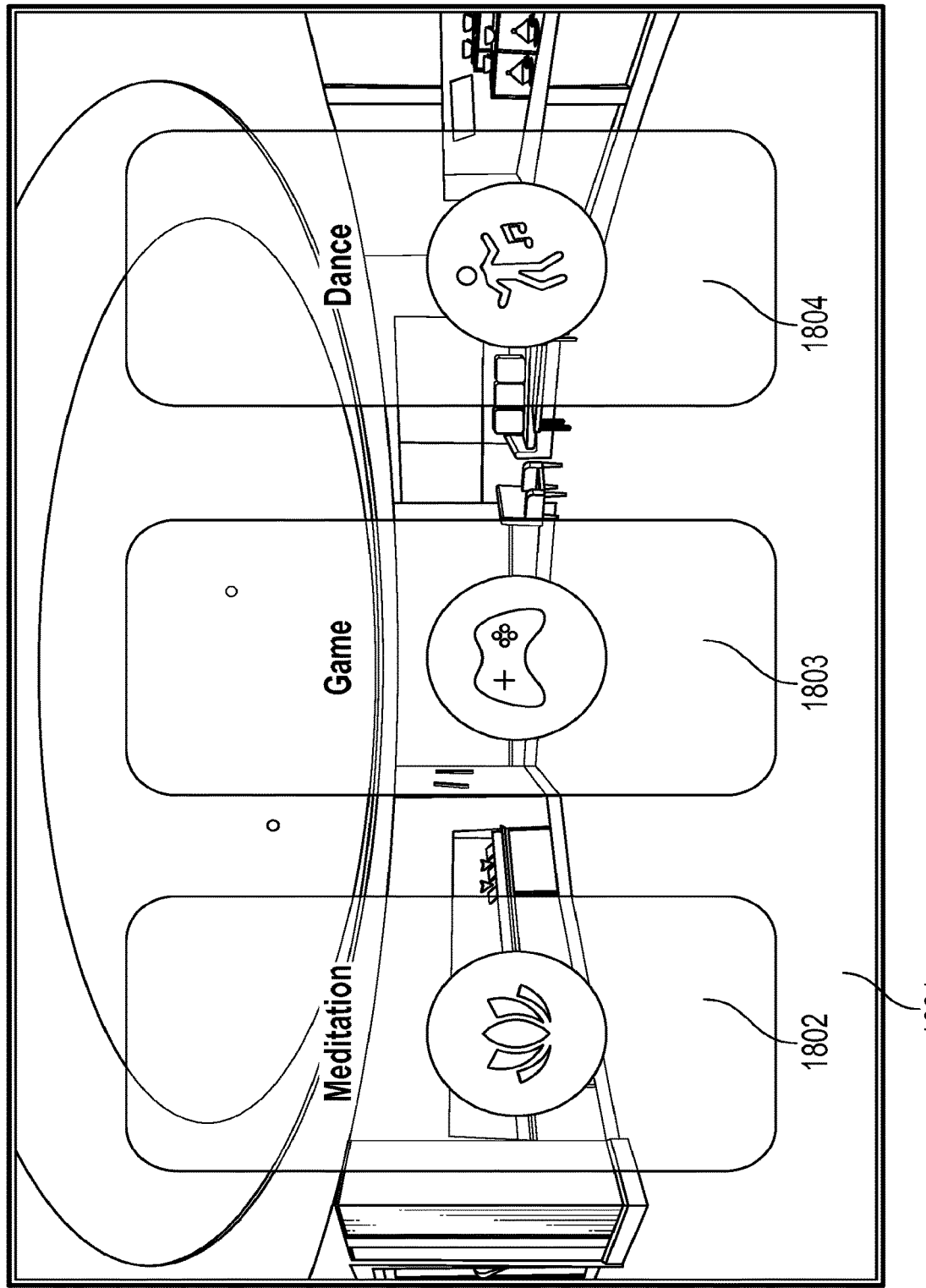
FIG. 18 depicts an exemplary user interface as may be generated by a headset (e.g., XR, VR, etc. headset), consistent with various exemplary aspects of one or more implementations of the disclosed technology.

2. Block Trial Diagram for Collecting Data—Experimental Paradigm a. Example UI in Mixed Reality for Selection of Element in the UI FIG. 18 depicts an exemplary user interface generated by an XR/VR/etc. headset, consistent with various exemplary aspects of one or more implementations of the disclosed technology. Referring to FIG. 18, an exemplary user interface 1801 is depicted, e.g., as generated by the system/component(s) herein such as those associated with an XR, VR or other headset, consistent with various exemplary aspects of one or more implementations of the disclosed technology. As shown in FIG. 18, an example user interface 1801, which may be two-dimensional (2D) or three-dimensional (3D), may be generated and employed to represent a series of options 1802, 1803, 1804, where each option may indicate a locus of attention of the user and therefore which element the user would like to select in the environment. Alternatively, other embodiments of a user interface, e.g., with differing objects, layouts and/or quantities of options, etc., may be presented to the user, and the alternate embodiments of a user interface will provide similar or comparable features, functionality and/or results.

Figure 19:
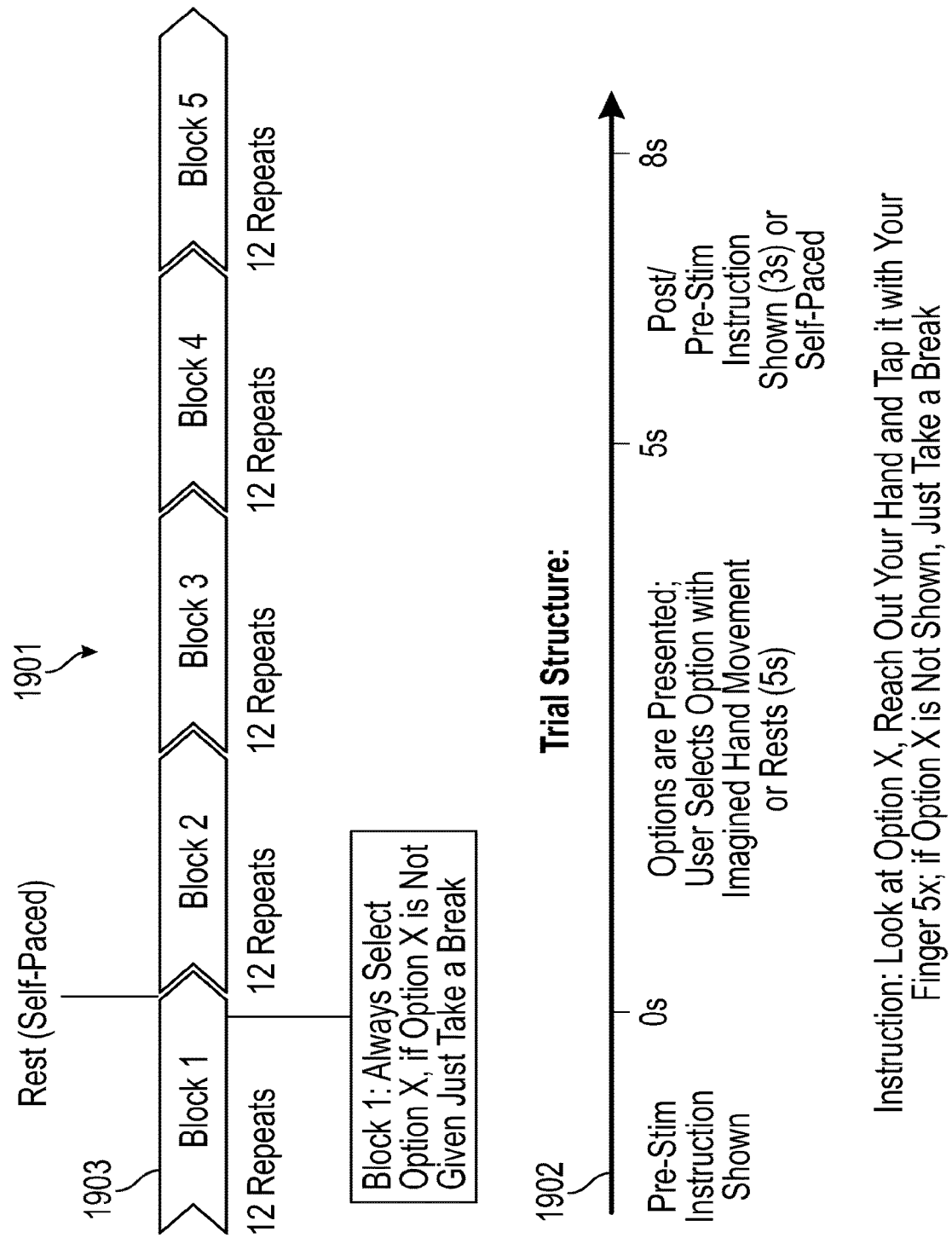
FIG. 19 depicts illustrative aspects of an exemplary data collection sequence detailing a representative process for conducting a series of trials, consistent with various exemplary aspects of one or more implementations of the disclosed technology.

FIG. 19 depicts illustrative aspects of one representative data collecting sequence 1901 including an exemplary trial structure or trial process for conducting a series of trials 1902, such as, e.g., those having exemplary option viewing only, versus those having option viewing with selection, consistent with various exemplary aspects of one or more implementations of the disclosed technology. According to certain embodiments including the example embodiment of FIG. 19, the overall structure of the data collecting sequence 1901 may be broken down into a number of blocks 1903, where, e.g. in some embodiments such as those using the example user interface shown in FIG. 18, each block 1903 may represent selection of one option, 1802, 1803, 1804 within the user interface 1801. Each block 1903 may further involve or reflect a number of trials 1902 conducted for selecting a specified option 1802, 1803, 1804. Each such trial 1902 may have a structure, such as the exemplary structure depicted in FIG. 19, which may include a pre-stimulation instruction shown before a timing sequence. According to some embodiments, for example, such pre-stimulation instruction may include or display instructions to look at one of a specified option 1802, 1803, 1804, e.g., to imagine or think about reaching out a hand and tapping the specified option 1802, 1803, 1804, or, alternatively, if the specified option 1802, 1803, 1804 is not shown, to take no action. The trial 1902 may proceed with presenting the user with options 1802, 1803, 1804 for five seconds, where the user then imagines or thinks about selecting the specified/desired option 1802, 1803, 1804 with hand movement, or, alternately, if the specified option 1802, 1803, 1804 is not shown, takes no action. Referring to the exemplary embodiment of FIG. 19, the period of time between when options are presented and when the user selects an option via imagined hand movement or the user rests, may last for about 5 seconds. Other time period may be utilized, such as 4 to 6 seconds, 3 to 7 seconds, 2 to 8 seconds, 3 to 8 seconds, and the like. In the exemplary implementation shown in FIG. 19, such trial 1902, which may serve as a training sequence or process, may conclude with a post-stimulation instruction (which, e.g., is indicated to last for 3 seconds in the exemplary embodiment of FIG. 19) or by offering a self-paced rest period in some embodiments.

According to aspects of the disclosed technology, each block 1903 in the data collecting sequence 1901 may correspond to selecting a different specified option 1802, 1803, 1804 from the user interface 1801. In some embodiments, each block 1903 may contain a fixed number of trials 1902 conducted for that block 1903. According to different embodiments, each block may contain a quantity of trails, such as a specified quantity, a quantity needed to establish a confidence level, or other benchmark quantity. In one illustrative embodiment, for example, each block 1903 may contain a distribution of half of the trials 1902 conducted while not displaying the specified option 1802, 1803, 1804 wherein the user takes no action, and half of the trials 1902 conducted while displaying the specified option 1802, 1803, 1804 wherein the user imagines picking the appropriate option. According to various embodiments, the distribution of the quantity of trials wherein the specified option 1802, 1803, 1804 are present versus the quantity of trials wherein the specified option 1802, 1803, 1804 are not present may also otherwise differ or vary.

While the above examples have been described, it is hereby noted that other structures for trials and data collecting sequences may be utilized consistent with systems and methods of data collection and the disclosed technology, e.g., to provide similar or comparable features, functionality and/or results. Among other things, for example, alternate time intervals may be selected or utilized to achieve results consistent with the disclosed technology, and alternate instructions may be provided while still accomplishing the desired data collection and/or other objectives of the present inventions.

Figure 20:
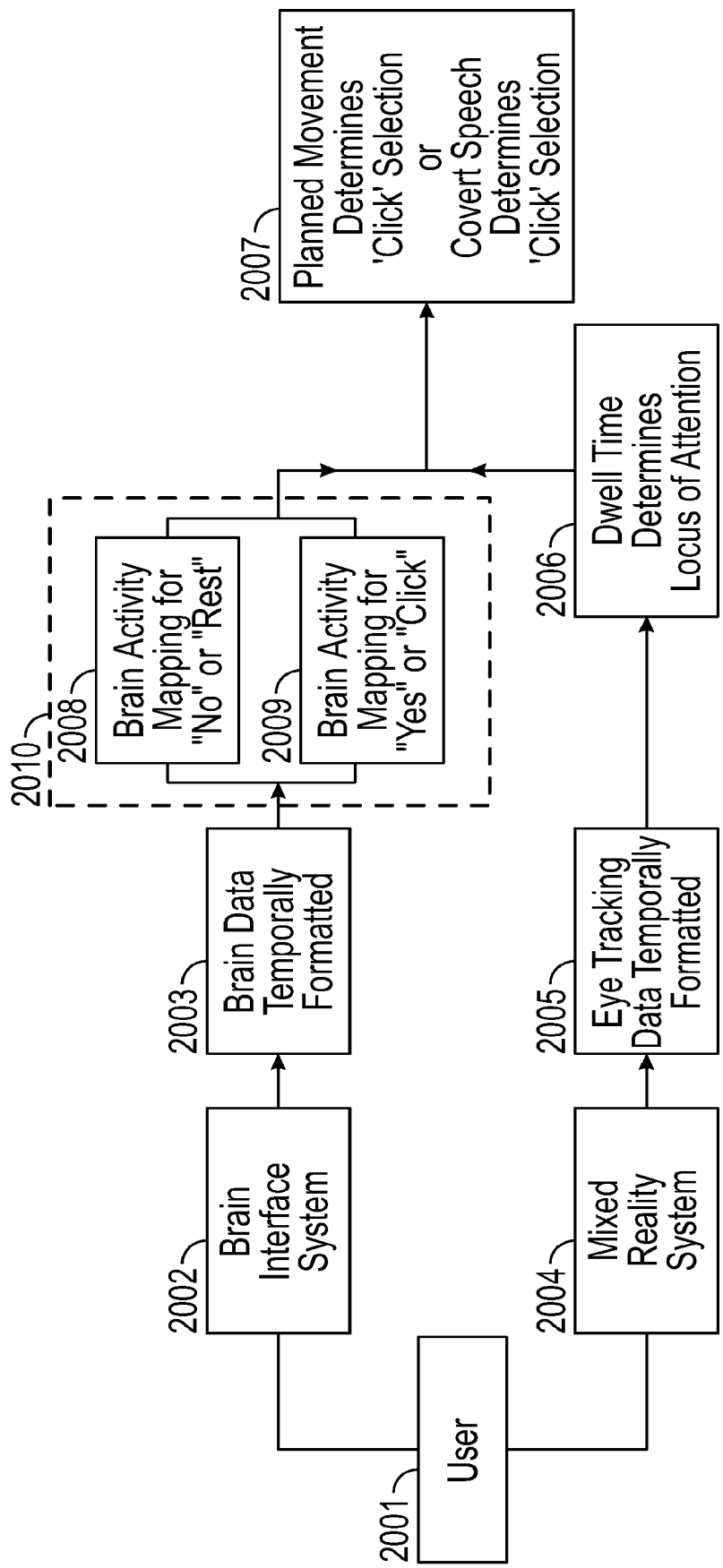
FIG. 20 depicts an illustrative flow diagram detailing an exemplary process of using an XR, VR, and/or other headset in combination with a BCI to initiate a "click" selection in a VR/XR environment, such as by anticipating planned movement or speech, consistent with various exemplary aspects of one or more implementations of the disclosed technology.

3. Process Map for Mechanism to Enable Selection of Elements in a UI Involving Combination(s) of Eye Tracking and Brain/Brain Interface Data FIG. 20 depicts an illustrative flow diagram detailing one exemplary process of using an XR, VR and/or other headset in combination with a BCI to initiate a selection (e.g., "click", etc.) in an XR/VR/etc. environment, such as by determining/anticipating planned movement or speech, consistent with various exemplary aspects of one or more implementations of the disclosed technology. Referring to FIG. 20, in one exemplary embodiment, the BCI System 2002 may be utilized to collect brain data via a brain interface system, at 2002, and then temporally format the brain data, at 2003. In parallel, an XR, VR, mixed reality and/or other such system may, at 2004, be utilized to collect eye tracking data, and then temporally format such eye tracking data, at 2005. Both data sets temporally formatted (at 2003 and 2005) may be collected from the data collecting sequence 1901 conducted through the trials 1902, e.g., via methods of using a VAE and computer, such as those described above in connection with FIGS. 12A through 15, and elsewhere herein.

a. BCI System 2002
i. Temporal Formatting of Brain Data 2003

The temporal formatting of brain data, at 2003, may occur, in some embodiments, in the context or embodiments consistent with FIG. 14A. FIG. 14A depicts an exemplary process flow associated with processing brain data (e.g., from a BCI interface, etc.) and converting such brain data to compressed images in the latent space. In connection with, or similar to, such processing, systems and methods herein may format the brain data with temporal/timing information that enables determination of precise timing or overlap with corresponding eye tracking data. Here, e.g., referring to FIG. 14A, a variational autoencoder 1203 may encode the BCI data 1401, e.g., from a BCI 1201, to the computing component 1204 in latent space 1407. As explained above, such latent space 1407 is a theoretical representation of the process of transforming and compressing the raw data (e.g., here, the brain data 1401), such as output from the BCI 1201, to the images in a specified format, or the representations in a 1st latent space, i.e., latent space 1 (1403). In other embodiments, the images generated may be in a format other than the format specified above. Turning to the temporal formatting of the brain data 2003, the brain data is temporally formatted such that it may be compared/mapped against eye-tracking and/or other objective measurements and data, such as obtained via the XR, VR, and/or other headsets herein. Such temporal formatting is important, as precise interrelationship(s) regarding timing of the changes in brain data, as compared to the eye tracking data, enables accurate determination of user selections or "clicks" of images that are viewed.

According to embodiments of the disclosed technology, temporal formatting of brain data, as here, refers to the use of time stamping or other such time formatting/aligning techniques to align the different data streams, for example, an eye tracking data stream, a brain recording data stream, which may itself be split into optical brain measurements and electrical brain measurements such as from EEG or ECOG, and other peripheral data streams such as heart rate, perspiration measurements, electrooculography measurements and kinematic measurements derived from any number of motor recording devices such as 3D movement scanners or muscle activation recorders, other signals and data streams set forth herein, and/or comparable signals/ streams. In a representative embodiment, e.g., one straightforward manifestation of this is to use existing time stamping software that comes with eye tracking devices, along with a timer which starts as a user enters a Unity/Unreal (AR/VR) experience. With such information, systems and methods herein may then align the passage of time in the Unity experience, with eye movements and also with brain activity. Here, for example, in an illustrative sequence, a user may encounter a red box at 3 seconds into an experience. By manually or automatically aligning the data streams, implementations herein can determine at which point an increase or decrease in brain activity in a specific brain region corresponds with visualizing or interacting with the red box and/or with user specific eye movements, gaze changes or pupillometric changes or kinematic measurements.

In further embodiments, the disclosed technology may utilize a multitude of methods to successfully implement temporal formatting of the data and/or align important events across multiple data streams. One such method is supervised neural decoding, which requires that the data be labeled. According to certain implementations, such labeling aspect may be done as per the above description, where manual timestamps are added and a timer is used for the user in the virtual experience. Next, the data and the true labels are then fed into a neural network for classification for the intended result, e.g., classification of the user's visual attention. However, one disadvantage of such processing is that it can often times be laborious to acquire the data labels and in addition, it is not always applicable in real world scenarios or can be difficult to achieve. Yet another method that embodiments herein may employ or involve is unimodal self-supervised neural decoding. Here, only the neural data stream (the data stream derived from the brain-recording/ brain-interface hardware) is present. So, rather than have the events manually labelled in the neural data stream, a neural network is deployed to automatically create the timestamps or labels. Such embodiments may be implemented by feeding the data into a specific neural network such as a convolutional neural network, which learns to separate the input data automatically into clustered features as the outputs (automated feature extraction). According to systems and methods, here, the clustered features may then be utilized as pseudo-labels which are fed back into the neural network in its training process. This, therefore, obviates the need for manual labelling of the data. One consideration of unimodal self-supervised neural decoding, though, is that accuracy levels do not always reach that of the supervised decoding.

Consistent with the disclosed technology, given the use of multiple data streams (eye tracking+multiple different brain recording streams in the multimodal interface+other peripheral data streams), a third technique may also be leveraged which is cross-modal self-supervised neural decoding. While such cross-modal self-supervised models have been demonstrated in other contexts with unlabeled audio and video data, it has not previously been used in neural decoding for visual attention and in brain-interfacing. In neural decoding with additional data streams, each data stream will have its own variability, however, consistent with systems and methods herein, behaviorally relevant activity is detected and determined as relevant in multiple data streams, e.g., assuming each one is acquired at a similar timescale and contains info related to behaviors of interest. This means, according to the disclosed technology, that sharing info across the different data streams enables robust training of the neural decoder.

In relevant embodiments, here, cross-modal deep clustering works by using a decoder model for each different data stream. As such, each decoder for each data stream may be trained using pseudo-labels that have been generated from the deep clusters derived from the data stream (same as the unimodal deep clustering above), but instead of using pseudo-labels from its own data stream, the pseudo-labels are selected or randomly selected from all other data streams except itself. This technology performs well and reduces overfitting due to variations between the different data streams which are all relevant to the task. Further, in addition to randomly sharing pseudo-labels for the multiple data streams, it is also possible to weight each data stream based on its reliability and data quality and to use data augmentations to further improve performance. In some instances, the decoder model used for such implementations, here, may include or involve a number of different architectures and may include convolutional neural networks. Overall, according to embodiments herein, such systems and methods of 'temporal formatting' may be implemented by first minimizing the loss function associated with the decoder, in a similar way to done in conventional supervising decoding. Second, the model's outputs may be segmented by an algorithm, such as the Sinkhorn-Knopp or comparable algorithm, into a certain number of clusters, which are then used as pseudo-labels. In some implementations, the number or quantity of clusters may be determined a priori by a human user.

b. Mixed Reality (MR/VR/AR/Etc) System Processing 2004 i. Temporal Formatting of Eye Tracking Data 2005

The temporal formatting of eye-tracking data, at 2005, may occur, in some embodiments, in the context or embodiments consistent with FIG. 14B. FIG. 14B depict exemplary process flows associated with processing eye tracking data and converting the data to compressed images in the latent space. Referring to FIG. 14B, a variational autoencoder 1203 may encode the eye tracking data 1404 from the headset 1202 user interface in latent space 1407, such as latent space 2 (1406) in FIG. 14B. Turning to the temporal formatting of the eye-tracking, at 2005, the eye tracking data is temporally formatted such that it may be compared/mapped against brain data other objective measurements/data derived from the brain signals, such as obtained via whatever BCI hardware is utilized. Such temporal formatting is important, as precise interrelationship(s) regarding timing of the changes in eye tracking data, as compared to the brain data, enables accurate determination of user selections or "clicks" of images that are viewed. Additional details of such temporal formatting features and functionality are set forth above.

Dwell time and determining locus of attention to cue a selection/"click" 2006

Referring again to the exemplary embodiment of FIG. 20, the eye tracking or mixed reality (XR, VR, etc.) device may provide a gaze direction (e.g., X-Y coordinate position, or other positional or vector information). Further, the eye tracking data may include a length of time the user's gaze was directed at an image, or dwell time. Here, for example, in some embodiments, systems and methods herein may record dwell times of between about 70 and about 500 milliseconds, or between about 90 and about 480 milliseconds, or between about 110 and about 460 milliseconds, or between about 130 and about 440 milliseconds, or between about 150 and about 420 milliseconds, or within combinations of such ranges/parameters, in certain embodiments. According to implementations herein, such gaze direction and dwell time may be captured for each trial 1902 of the data collecting sequence 1901.

According to embodiments herein, both gaze direction and dwell times may be collected for trials 1902 in which the specified option(s) 1802, 1803, 1804 were either presented to the user or were not presented to the user, wherein the dwell time, along with gaze position or gaze direction information of the user in some embodiments, may be utilized to determine the locus of attention, at 2006. Consistent with implementations of the disclosed technology, the difference in dwell times and gaze direction(s) for when options 1802, 1803, 1804 were presented, versus when they are not presented, may be utilized to determine the locus of attention 2006, such as by matching a threshold value that indicates when a selection has been made via the user's gaze.

Further, as noted above, dwell times other than between 70 ms and 500 ms may be utilized/recorded and may be used to approximate the locus of attention 2006, and such differing dwell times may provide similar or comparable functionality and/or results, according to certain embodiments. Alternatively, different embodiments of a user interface 1801 as well as other layouts and/or quantities of options may be displayed to the user, and various such alternate embodiments of a user interface 180 may accomplish similar results and/or may be used to function in a similar way.

c. Planned Movements Mapped and Determine Selection/Click 2007

Further, referring again to FIG. 20, the temporally formatted brain data 2003 may provide saliency mapping or thresholds for brain activity for planned movements of the user, as recorded or collected for the trials 1902, e.g., where the specified option(s) 1802, 1803, 1804 were either presented to the user or not presented to the user. As such, according to some embodiments, a user's imagined motor movement may be detected and decoded from brain data sensors positioned to monitor corresponding motor areas of the brain, where such planned movement may determine the user selection or click, at 2007. This functionality may be utilized, for example, when the user is instructed to imagine tapping a desired selection (i.e., options 1802, 1803, 1804) when it is displayed on the user interface. Advantageously, here, such decoder or decoding needs to only distinguish between such imagined movement (user-imagined tapping of a desired option when it is displayed) and a rest or no-action state (option not displayed, so no action imagined).

a. Covert Speech is Mapped and Determines Selection/Click 2007

In other alternative embodiments, a single imagined speech command such as "yes" or "select," referred to herein as covert speech, may be utilized. Here, for example, the temporally formatted brain data 2003 may provide saliency mapping or thresholds corresponding to desired brain activity, such that a decoder is able to distinguish between brain activity when a user imagines such predefined or known speech when the specified option 1802, 1803, 1804 is presented and brain activity when a user 2001 does not imagine speech, i.e., when the specified option 1802, 1803, 1804 is not presented.

Further, in still other embodiments, a premotor signal may be utilized via placement of one or more sensors to detect regions of the mind/brain indicative of premotor activity, stemming from the user's planning of a movement. To the user, such signals do not even correspond to any feeling like the user is intending to move. Instead, given only the natural intention of the user to select something in augmented reality or on a UI, a signal in such premotor regions is generated and obtainable. According to such alternative embodiment, a user's brain activity may be mapped in saliency mapping, or a threshold may be determined during the trial(s), regarding brain activity associated with premotor signals emitted by the user's brain.

Optional element 2010 in FIG. 20, simply illustrates an optional state where the brain activity may be mapped or decoded to reflect the understood desire of the user, such as a "Yes" or "Click" desire or instruction, at 2009, or a "No" or "Rest" instruction, at 2008. Such information may then be utilized, along with the locus of attention information at 2006, to determine the user's planned movement or planned speech in order to make a final selection, at 2007, based on the user's imaginative or planned action or imaginative or planned speech.

According to still further exemplary embodiments herein, the user interface 1801 may additionally couple the successful selection of an option 1802, 1803, 1804 with some visual display indicia or element, such as a loading circle or a colored border filling up around a UI element corresponding to the desired/selected option 1802, 1803, 1804, i.e., as the user is directing their focus thereon. Alternatively or additionally, other graphical indications may be displayed, for example, the user interface 1801 may enlarge or change the appearance of the option 1802, 1803, 1804, and/or play a sound upon the successful selection thereof.

4. Using Brain Datastream(s) for Determining Both the Locus of Attention and the Determination of Selection Versus No Selection.

Figure 21:
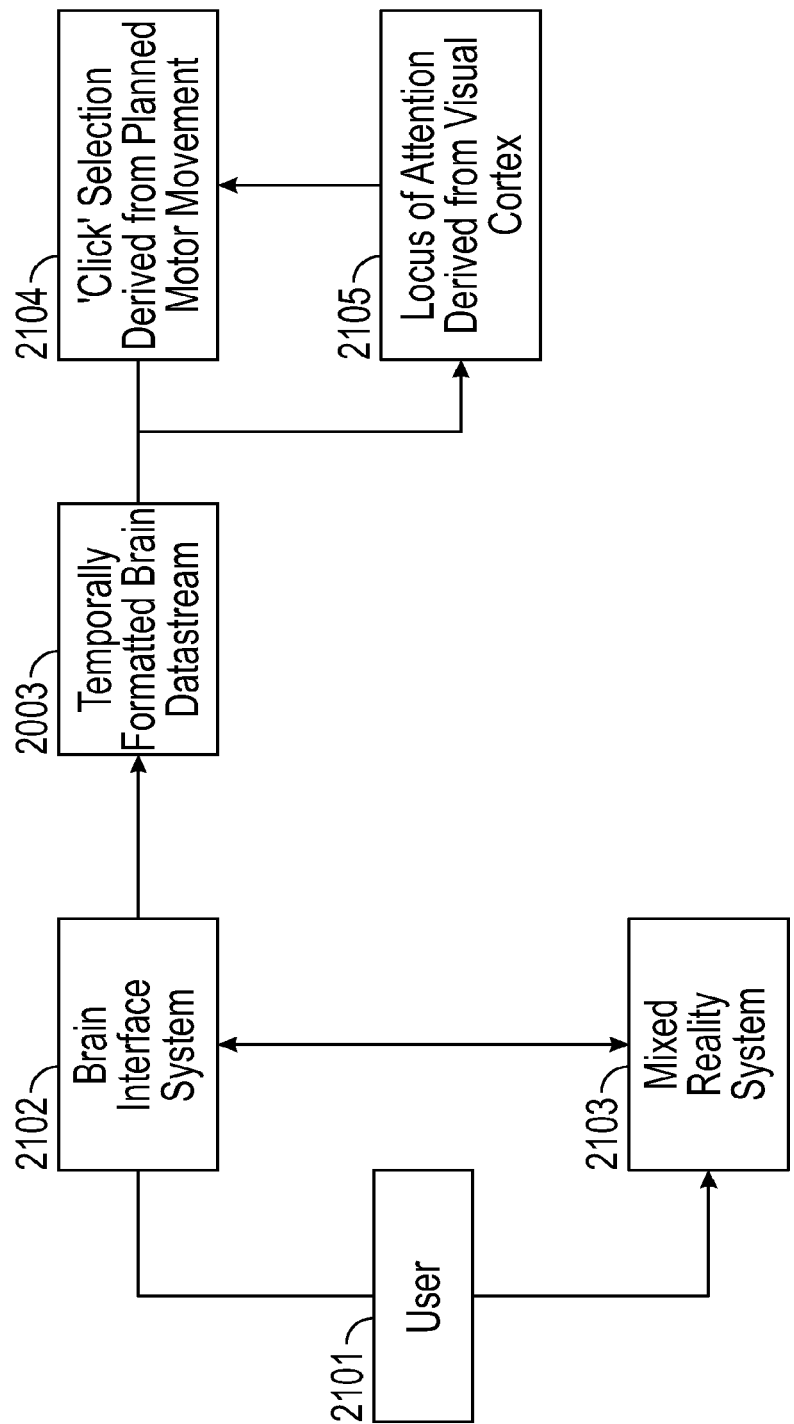
FIG. 21 depicts an illustrative flow diagram detailing an exemplary process of using only temporally formatting brain data 2003 to initiate a selection or "click", consistent with various exemplary aspects of one or more implementations of the disclosed technology.

FIG. 21 depicts an illustrative flow diagram detailing an exemplary process of using only temporally formatting brain data 2003 to initiate a selection or "click", consistent with various exemplary aspects of one or more implementations of the disclosed technology. Referring to FIG. 21, such temporally formatted brain data 2003 derived from brain interface system 2102 and/or mixed reality system 2103 may be used to anticipate planned motor movement, at 2104, and may also be used to derive a locus of attention of user 2101, at 2105, e.g., based on visual cortex information. According to such embodiments, systems and methods herein may enable selecting elements on a UI using just brain data to determine both a locus of attention as well as a user's desired selection or "click."

Further, it is noted here that the planned motor movement for the selection or click may be determined from a brain-recording device data stream that is separate to that from the locus of attention determining device. In some embodiments, the locus of attention may be determined from both eye gaze data and brain-recording device data streams from the visual cortex, e.g., using a cross-modal deep clustering method described above in some implementations. One exemplary set of steps that may be performed in order to reproduce the results might then be as follows: (1) data is recorded from the brain-recording device whilst the user is engaged in a mixed reality experience; (2) data streams are separated based on, e.g., area of the brain/electrode, optode placement and/or recording device; (3) cross-modal or uni-modal deep clustering or supervised labelling is used to temporally format the data streams and provide labels of events in the mixed reality experience that correspond to the brain activity fluctuations; (4) the pseudo-labeled or manually labeled data is then used by a classifier to determine the locus of attention; (5) upon derivation of the locus of attention, the pseudo-labeled data is then used by an alternative classifier to determine an intended movement and therefore a 'click' to activate selection of the intended UI element in the mixed reality experience.

Figure 22:
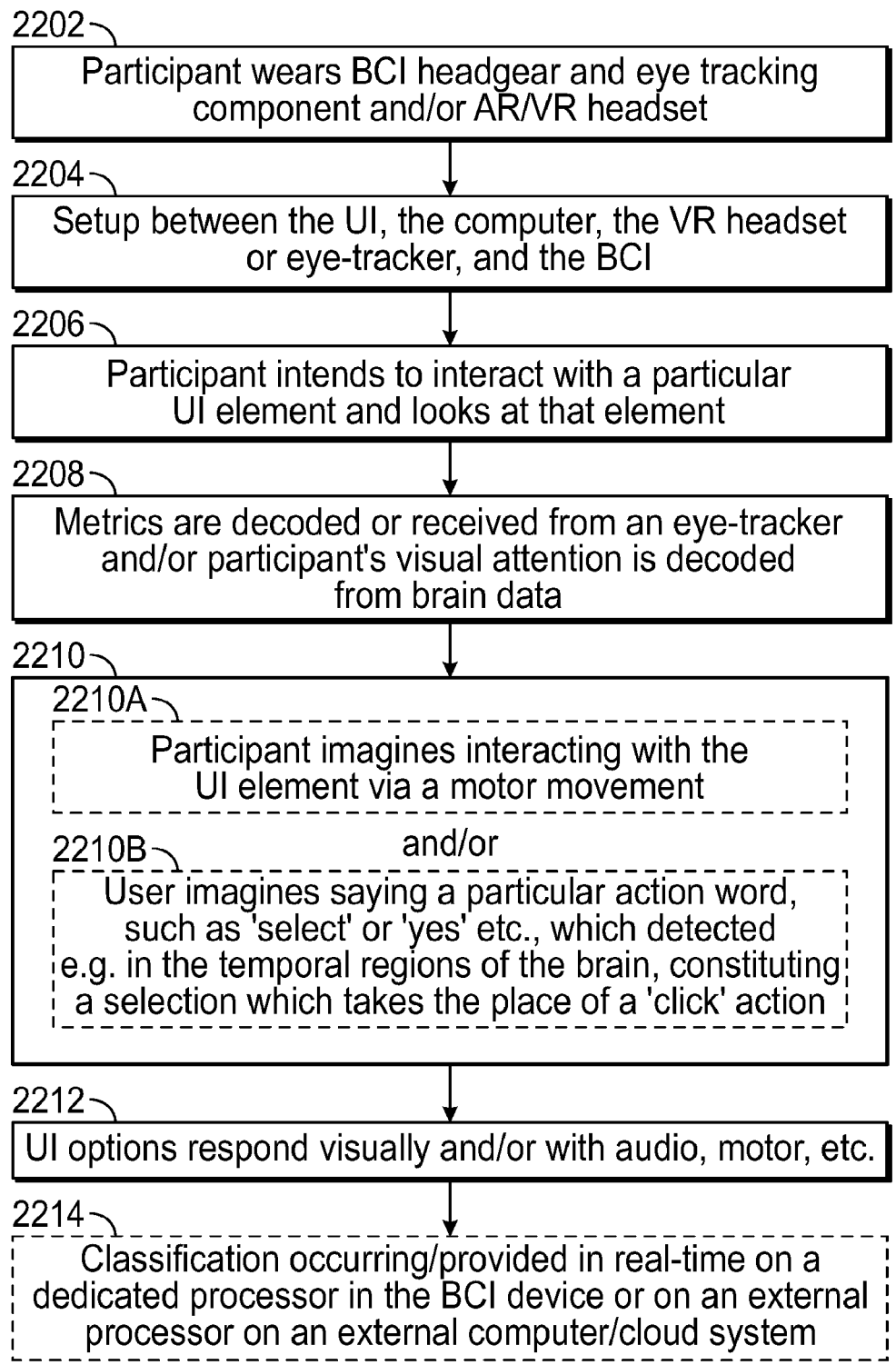
FIG. 22 depicts an illustrative flow diagram detailing one exemplary process of using BCI headgear along with eye tracking and/or a XR/VR/etc. headset to generate a mind-initiated selection of an option, such as via a virtual, extended, mixed reality and/or other such environment or interface, consistent with various exemplary aspects of one or more implementations of the disclosed technology.

FIG. 22 depicts an illustrative flow diagram detailing one exemplary process of using BCI headgear along with eye tracking and/or a XR/VR/etc. headset to generate a brain- or mind-initiated selection of an option, such as via a virtual, extended, mixed reality and/or other such environment or interface, consistent with various exemplary aspects of one or more implementations of the disclosed technology. Prior to the illustrative flow process shown in FIG. 22, various trials would have been performed or corresponding known user data otherwise obtained for the participant, to provide the system of knowledge regarding both the user's eye movements, determined through the eye tracking software and/or hardware, and recordings of the user's brain activity via a BCI to establish thresholds and other parameters or BCI hardware signal information to determine when the participant was making selections.

Referring to the exemplary process of FIG. 22, a participant may first wear a BCI headgear and XR/VR/etc headset with eye tracking hardware and/or software components, at 2202. Next, at 2204, a setup process may be performed to integrate the user interface, the computer, the XR/VR/etc. headset, and the brain computer interface for operation. As a result, the system is configured to display various UI images and elements to the participant. At 2206, the participant then intends to interact with a particular UI element and looks or gazes at that UI element. Eye tracking and brain data is then processed, at 2208, wherein dwell time metrics may be decoded from the eye-tracking data and/or the participant's visual attention may be decoded from the brain data, e.g., via a saliency map derived from the brain data during the trials.

Next, at 2210, the participant then imagines interacting with the UI element of interest, which may take the form of one or more imaginary interactions. For example, in one imaginary interaction, at 2210A, the participant imagines interacting with the UI element via a motor movement. Here, without actually carrying out the movement, the user's planned action is decoded from the brain data, e.g., in the pre-motor areas. As a further imaginary interaction, at 2210B, the user may imagine saying a particular action word (such as 'select', 'yes,' etc.), which, when detected in the temporal regions of the brain, constitutes or corresponds to a selection that takes the place of a 'click' action. Either way, the decoded intention takes the place of the 'click' action. Upon determination that a selection has been made, the system and/or UI may respond with UI option or elements that graphically or visually confirm the selection and/or with an audio indication (e.g., noise, ping, etc.), a tactile indication (e.g., vibration, etc.) or other such known indications, at 2212. As one example of such indication, while the participant is looking at the option, a circle can begin to fill, and then when the participant makes the selection, it glows and/or expands, or the like. Finally, related classification of the selection may then occur or be provided in real-time on a dedicated processor associated with the BCI device and/or on an external processor on an external computer/cloud system, at 2214.

As described above, the systems and methods described herein may, in some embodiments, detect a user's intent to move and perform a suitable UI interact action (such as the 'click' action described above) in response. The process of voluntary movement begins in the prefrontal and parietal areas, where the intention to move is generated. This intention is then transmitted to the primary motor cortex, which is responsible for planning and executing actions. The primary motor cortex receives input from other areas of the brain, such as the somatosensory cortex, which provides information about the position and movement of the body's limbs and joints. This information, combined with the intention to move, generates signals that coordinate the activity of motor neurons. Monitoring of a user's nervous system in order to predict their intent to move is sometimes referred to as motor imagery, or 'MI'.

During the generation of the intention to move, multiple functional areas of the brain coordinate their physiological activities, resulting in neural electrical signals. In addition, due to neurovascular coupling, the concentration of brain haemoglobin changes. These physiological signals can be detected and analyzed through various BCI systems, including the BCI systems discussed above. Detection and analysis of these signals can enable BCI systems to detect a user's intention to move at the level of the central nervous system.

After the raw signals are retrieved by the devices, algorithms play a crucial role in transforming the raw data into meaningful information for real-time communication and control. These algorithms can be broadly classified into four categories: preprocessing, feature extraction, feature selection, and classification.

The preprocessing stage aims at reducing noise, artefacts, and irrelevant information from the raw signals. Common techniques used for EEG preprocessing include band-pass filtering to focus on specific frequency bands (e.g., delta, theta, alpha, beta, gamma) and artefact removal (Independent Component Analysis (ICA), Principal Component Analysis (PCA)) to mitigate the artefact interference. Additionally or alternatively, signals from a given channel (e.g., a channel that detects to a depth of 21 mm, or the human skull, as discussed above) can be subtracted out from channels that detect signals from deeper inside a user's head to effectively filter out the signals being received at the shallower depths.

Feature extraction techniques are employed to transform the preprocessed signals into feature vectors, which can be used to identify different mental states or cognitive tasks. For EEG signals, common methods include time-domain (Hjorth parameters, Autoregressive (AR) coefficients), frequency-domain (spectral power, coherence), and time-frequency domain (wavelet transform, Hilbert-Huang transform) features.

Feature selection methods help in identifying the most relevant features for the task at hand, leading to improved classification performance and reduced computational complexity. Common feature selection techniques include filter methods (correlation, mutual information), wrapper methods (forward, backward, recursive feature elimination), and embedded methods (LASSO, Ridge Regression).

At the end of the decision system, the selected features are fed into a classification algorithm, which determines the motion intention from the user. Popular classifiers for BCI systems include classical machine learning models (linear discriminant analysis (LDA), support vector machines (SVM), and artificial neural networks (ANN)) and deep learning models (convolutional neural networks (CNN), long short-term memory (LSTM), and transformer).

Overall Implementations of the Disclosed Technology

According to the above such technology, systems and methods herein may be utilized to detect and/or involve detection of at least haemodynamic signals and direct neuronal signals (fast optical signals) that both correspond to neural activity, simultaneously. In some embodiments, for example, the disclosed technology may leverage fast optical signals for brain-computer interfacing, whereas no existing device (combined with the above features and/or functionality, or otherwise) leverages both fast optical signals (FOS) and haemodynamic signals (which may be obtained, e.g., via near-infrared spectroscopy, NIRS), simultaneously, for brain-computer interfacing nor does any existing device use fast optical signals alone for brain-interfacing applications.

While the above disclosure sets forth certain illustrative examples, such as embodiments utilizing, involving and/or producing fast optical signal (FOS) and haemodynamic (e.g., NIRS, etc.) brain-computer interface features, the present disclosure encompasses multiple other potential arrangements and components that may be utilized to achieve the brain-interface innovations of the disclosed technology. Some other such alternative arrangements and/or components may include or involve other optical architectures that provide the desired results, signals, etc. (e.g., pick up NIRS and FOS simultaneously for brain-interfacing, etc.), while some such implementations may also enhance resolution and other metrics further.

Among other aspects, for example, implementations herein may utilize different optical sources than those set forth, above. Here, for example, such optical sources may include one or more of: semiconductor LEDs, superluminescent diodes or laser light sources with emission wavelengths principally, but not exclusively within ranges consistent with the near infrared wavelength and/or low water absorption loss window (e.g., 700-950 nm, etc.); non-semiconductor emitters; sources chosen to match other wavelength regions where losses and scattering are not prohibitive; here, e.g., in some embodiments, around 1060 nm and 1600 nm, inter alia; narrow linewidth (coherent) laser sources for interferometric measurements with coherence lengths long compared to the scattering path through the measurement material (here, e.g., (DFB) distributed feedback lasers, (DBR) distributed Bragg reflector lasers, vertical cavity surface emitting lasers (VCSEL) and/or narrow linewidth external cavity lasers; coherent wavelength swept sources (e.g., where the center wavelength of the laser can be swept rapidly at 10-200 KHz or faster without losing its coherence, etc.); multiwavelength sources where a single element of co packaged device emits a range of wavelengths; modulated sources (e.g., such as via direct modulation of the semiconductor current or another means, etc.); and pulsed laser sources (e.g., pulsed laser sources with pulses between picoseconds and microseconds, etc.), among others that meet sufficient/proscribed criteria herein.

Implementations herein may also utilize different optical detectors than those set forth, above. Here, for example, such optical detectors may include one or more of: semiconductor pin diodes; semiconductor avalanche detectors; semiconductor diodes arranged in a high gain configuration, such as transimpedance configuration(s), etc.; single-photon avalanche detectors (SPAD); 2-D detector camera arrays, such as those based on CMOS {complementary metal oxide semiconductor} or CCD {charge-coupled device} technologies, e.g., with pixel resolutions of 5×5 to 1000×1000; 2-D single photon avalanche detector (SPAD) array cameras, e.g., with pixel resolutions of 5×5 to 1000×1000; and photomultiplier detectors, among others that meet sufficient/ proscribed criteria herein.

Implementations herein may also utilize different optical routing components than those set forth, above. Here, for example, such optical routing components may include one or more of: silica optical fibre routing using single mode, multi-mode, few mode, fibre bundles or crystal fibres; polymer optical fibre routing; polymer waveguide routing; planar optical waveguide routing; slab waveguide/planar routing; free space routing using lenses, micro optics or diffractive elements; and wavelength selective or partial mirrors for light manipulation (e.g. diffractive or holographic elements, etc.), among others that meet sufficient/proscribed criteria herein.

Implementations herein may also utilize other different optical and/or computing elements than those set forth, above. Here, for example, such other optical/computing elements may include one or more of: interferometric, coherent, holographic optical detection elements and/or schemes; interferometric, coherent, and/or holographic lock-in detection schemes, e.g., where a separate reference and source light signal are separated and later combined; lock in detection elements and/or schemes; lock in detection applied to a frequency domain (FD) NIRS; detection of speckle for diffuse correlation spectroscopy to track tissue change, blood flow, etc. using single detectors or preferably 2-D detector arrays; interferometric, coherent, holographic system(s), elements and/or schemes where a wavelength swept laser is used to generate a changing interference patter which can be analyzed; interferometric, coherent, holographic system where interference is detected on, e.g., a 2-D detector, camera array, etc.; interferometric, coherent, holographic system where interference is detected on a single detector; controllable routing optical medium such as a liquid crystal; and fast (electronics) decorrelator to implement diffuse decorrelation spectroscopy, among others that meet sufficient/proscribed criteria herein.

Implementations herein may also utilize other different optical schemes than those set forth, above. Here, for example, such other optical schemes may include one or more of: interferometric, coherent, and/or holographic schemes; diffuse decorrelation spectroscopy via speckle detection; FD-NIRS; and/or diffuse decorrelation spectroscopy combined with TD-NIRS or other variants, among others that meet sufficient/proscribed criteria herein.

Implementations herein may also utilize other multichannel features and/or capabilities than those set forth, above. Here, for example, such other multichannel features and/or capabilities may include one or more of: the sharing of a single light source across multiple channels; the sharing of a single detector (or detector array) across multiple channels; the use of a 2-D detector array to simultaneously receive the signal from multiple channels; multiplexing of light sources via direct switching or by using "fast" attenuators or switches; multiplexing of detector channels on to a single detector (or detector array) via by using "fast" attenuators or switches in the routing circuit; distinguishing different channels/multiplexing by using different wavelengths of optical source; and distinguishing different channels/multiplexing by modulating the optical sources differently, among others that meet sufficient/proscribed criteria herein.

As disclosed herein, implementations and features of the present inventions may be implemented through computer-hardware, software and/or firmware. For example, the systems and methods disclosed herein may be embodied in various forms including, for example, one or more data processors, such as computer(s), server(s), and the like, and may also include or access at least one database, digital electronic circuitry, firmware, software, or in combinations of them. Further, while some of the disclosed implementations describe specific (e.g., hardware, etc.) components, systems, and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various processes and operations according to the inventions or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the inventions, or it may be more convenient to construct a specialized apparatus or system to perform the required methods and techniques.

In the present description, the terms component, module, device, etc. may refer to any type of logical or functional device, process or blocks that may be implemented in a variety of ways. For example, the functions of various blocks can be combined with one another and/or distributed into any other number of modules. Each module can be implemented as a software program stored on a tangible memory (e.g., random access memory, read only memory, CD-ROM memory, hard disk drive) within or associated with the computing elements, sensors, receivers, etc. disclosed above, e.g., to be read by a processing unit to implement the functions of the innovations herein. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

Aspects of the systems and methods described herein may be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy logic, neural networks, other AI (Artificial Intelligence) or machine learning systems, quantum devices, and hybrids of any of the above device types.

It should also be noted that various logic and/or features disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in tangible various forms (e.g., optical, magnetic or semiconductor storage media), though do not encompass transitory media.

Other implementations of the inventions will be apparent to those skilled in the art from consideration of the specification and practice of the innovations disclosed herein. It is intended that the specification and examples be considered as exemplary only, with a true scope and spirit of the inventions being indicated by the present disclosure and various associated principles of related patent doctrine.

The invention claimed is:

1. A computer-implemented method comprising:
monitoring, via a brain computer interface (BCI), brain data of a user associated with the user's interaction with GUI elements, the BCI being configured to detect brain activity of the user associated with the user's interaction with interface elements within an environment, the environment comprising GUI elements and at least one of a mixed reality environment or a 2D software environment;
recording gaze information associated with a gaze location of the user during interaction with the environment,
decoding brain data of the user in temporal conjunction with detecting, via the gaze information, the user's visual attention on a particular element of the environment;
determining, based on decoding the brain data of the user, an imagined action indicating that the user wishes to interact with the particular element of the environment; and
generating, in response to determining the imagined action indicating that the user wishes to interact with the particular element, an interaction event with the particular element of the environment.

2. The computer-implemented method of claim 1, wherein decoding the brain data comprises generating a saliency map of the user's visual attention from brain data from the brain computer interface.

3. The computer-implemented method of claim 1, wherein recording the gaze information associated with the gaze location of the user comprises receiving eye-tracking data from an eye-tracker component.

4. The computer-implemented method of claim 1, wherein determining the imagined action comprises determining, based on decoding the brain data of the user, an imagined motor movement of the user's body.

5. The computer-implemented method of claim 1, wherein determining the imagined action comprises determining an imagined spoken language command from the brain data.

6. The computer-implemented method of claim 1, wherein decoding the brain data of the user comprises:
creating, based on the brain data of the user, a brain-data saliency map by:
creating a plurality of brain data images that each represent at least one feature from the brain data mapped to at least one scalp location;
representing the brain data images in latent space by processing through a variational autoencoder;
generating, using a generator network, the brain-data saliency map based on the brain data images represented in latent space;
creating, based at least in part on the recorded gaze information, an eye-tracking saliency map by representing the recorded gaze information in latent space by processing through the variational autoencoder;
distinguishing, using a discriminator network, differences between the eye-tracking saliency map and the brain-data saliency map;
deriving, based on an output of the discriminator network, a loss function; and
modifying, based on a feedback loop that uses the loss function to inform modifications to the generator network, the generator network.

7. The method of claim 1, wherein determining the imagined action comprises at least one of:
detecting imagined speech, wherein the imagined speech comprises a word from a predetermined list of words that indicate intention to interact with user interface elements; or
detecting a premotor brain signal.

8. The method of claim 1, wherein determining the imagined action comprises detecting an imagined motor movement, wherein the imagined motor movement comprises an imagined physical interaction with the particular element of the environment.

9. The method of claim 8, wherein detecting the imagined motor movement comprises:
processing, by a decoder communicatively coupled to the BCI and configured to receive detected motor movement of motor areas, the brain data; and
distinguishing, by the decoder, between imagined movement of the user's body and a rest state of the user.

10. The method of claim 8, wherein detecting the imagined motor movement comprises detecting the imagined motor movement via electrodes placed on the user's scalp in proximity to a motor cortex of the user's brain.

11. The method of claim 1, recording the gaze information comprises processing the gaze of the user over a dwell time of 70-500 ms to determine a gaze direction.

12. The method of claim 1, wherein recording the gaze information comprises recording the gaze information by an augmented reality headset.

13. The method of claim 1, wherein the method further comprises:
recording the gaze and the brain activity of the user during a training period; and
training, based on data gathered during the training period, a classifier that detects imagined physical actions in the brain activity.

14. The method of claim 13, wherein determining the imagined action comprises detecting the imagined physical action via the classifier.

15. The method of claim 1, wherein the BCI is integrated into a mixed reality headset, the method further comprising:
monitoring the brain data of the user comprises monitoring the brain data of the user by the BCI that is integrated into the mixed reality headset;
recording the gaze information comprises monitoring the user's gaze by the mixed reality headset; and
displaying the environment to the user by the mixed reality headset.

16. The method of claim 1, wherein the BCI comprises a housing that is physically separate from a headset that displays the environment.

17. The method of claim 1, wherein generating the interaction event comprises visually transforming the element to indicate the interaction event.

18. The method of claim 1, further comprising:
detecting the user's visual attention on an additional element of the environment;
detecting a lack of the imagined action in the brain activity of the user in temporal conjunction with the user's visual attention on the additional element;
determining, based on the lack of the imagined action in temporal conjunction with the user's visual attention on the additional element, that the user does not intend to interact with the additional element; and refraining, in response to determining that the user does not intend to interact with the additional element, from generating an interaction event with the additional element.

19. A system comprising:
at least one physical computer processor;
a memory coupled to the at least one computer processor; and
one or more computing components comprising non-transitory computer readable media containing and/or configured to execute computer-readable instructions, the computer-readable instructions comprising instructions that, when executed by the at least one computer processor, cause the system to perform operations including:
monitoring, via a brain computer interface (BCI), brain data of a user associated with the user's interaction with GUI elements, the BCI being configured to detect brain activity of the user associated with the user's interaction with interface elements within an environment, the environment comprising GUI elements and a mixed reality environment;
recording the gaze and the brain activity of the user during a training period, wherein recording the gaze information comprises processing the gaze of the user over a dwell time of 70-500 ms to determine a gaze direction;
training, based on data gathered during the training period, a classifier that detects imagined physical actions in the brain activity;
recording gaze information associated with a gaze location of the user during interaction with the environment;
decoding brain data of the user in temporal conjunction with detecting, via the gaze information, the user's visual attention on a particular element of the environment;
determining, based on decoding the brain data of the user, an imagined action indicating that the user wishes to interact with the particular element of the environment, the determining the imagined action comprising detecting an imagined motor movement, which is comprised of an imagined physical interaction with the particular element of the environment, including:
detecting the imagined motor movement via electrodes placed on the user's scalp in proximity to a motor cortex of the user's brain;
processing, by a decoder communicatively coupled to the BCI and configured to receive detected motor movement of motor areas, the brain data; and
distinguishing, by the decoder, between imagined movement of the user's body and a rest state of the user; and
generating, in response to determining the imagined action indicating that the user wishes to interact with the particular element, an interaction event with the particular element of the environment.

20. One or more non-transitory computer-readable media containing and/or configured to execute computer-readable instructions, the computer-readable instructions comprising instructions that, when executed by one or more processors, cause the one or more processors to:
monitoring, via a brain computer interface (BCI), brain data of a user associated with the user's interaction with GUI elements, the BCI being configured to detect brain activity of the user associated with the user's interaction with interface elements within an environment, the environment comprising GUI elements and a mixed reality environment;
recording gaze information associated with a gaze location of the user during interaction with the environment,
decoding brain data of the user in temporal conjunction with detecting, via the gaze information, the user's visual attention on a particular element of the environment;
determining, based on decoding the brain data of the user, an imagined action indicating that the user wishes to interact with the particular element of the environment; and
generating, in response to determining the imagined action indicating that the user wishes to interact with the particular element, an interaction event with the particular element of the environment;
wherein the decoding the brain data of the user includes:
creating, based on the brain data of the user, a brain-data saliency map by:
creating a plurality of brain data images that each represent at least one feature from the brain data mapped to at least one scalp location;
representing the brain data images in latent space; and
generating the brain-data saliency map based on the brain data images represented in latent space;
wherein the method further comprises:
creating, based on the recorded gaze information, an eye-tracking saliency map by representing the recorded gaze information in latent space;
distinguishing, using a discriminator network, differences between the eye-tracking saliency map and the brain-data saliency map;
deriving, based on an output of the discriminator network, a loss function; and
modifying, based on a feedback loop that uses the loss function to inform modifications to the generator network, the generator network.

* * * * *